(12) United States Patent
Kim

(10) Patent No.: US 10,576,988 B2
(45) Date of Patent: Mar. 3, 2020

(54) BIOSIGNAL DETECTING DEVICE AND BIOSIGNAL DETECTING SYSTEM INCLUDING THE SAME

(71) Applicant: Electronics and Telecommunications Research Institute, Daejeon (KR)

(72) Inventor: Dong Kyoo Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 15/944,098

(22) Filed: Apr. 3, 2018

(65) Prior Publication Data

US 2019/0039623 A1    Feb. 7, 2019

(30) Foreign Application Priority Data

Aug. 2, 2017    (KR) .......................... 10-2017-0098258

(51) Int. Cl.
| | |
|---|---|
| *B60W 40/08* | (2012.01) |
| *G08B 21/06* | (2006.01) |
| *G08B 25/10* | (2006.01) |
| *A61B 5/05* | (2006.01) |
| *A61B 5/00* | (2006.01) |

(Continued)

(52) U.S. Cl.
CPC .............. *B60W 40/08* (2013.01); *A61B 5/05* (2013.01); *A61B 5/168* (2013.01); *A61B 5/18* (2013.01); *A61B 5/6893* (2013.01); *G08B 21/06* (2013.01); *G08B 25/10* (2013.01); *G08B 31/00* (2013.01); *A61B 5/0205* (2013.01); *A61B 5/02444* (2013.01); *B60W 2040/0827* (2013.01); *B60W 2040/0872* (2013.01)

(58) Field of Classification Search
CPC ......... B60W 40/08; B60W 2040/0827; B60W 2040/0872; A61B 5/0205; A61B 5/02444; G08B 21/06; G08B 25/10; G08B 31/00
USPC ......................................................... 340/439
See application file for complete search history.

(56) References Cited

U.S. PATENT DOCUMENTS

| | | | |
|---|---|---|---|
| 6,179,378 B1 * | 1/2001 | Baumgartner | B60N 2/002 280/735 |
| 6,684,973 B2 | 2/2004 | Baba et al. | |

(Continued)

FOREIGN PATENT DOCUMENTS

| | | |
|---|---|---|
| JP | 201668841 A | 5/2016 |
| JP | 2016168177 A | 9/2016 |
| KR | 1020140024606 A | 3/2014 |

*Primary Examiner* — Omar Casillashernandez
(74) *Attorney, Agent, or Firm* — William Park & Associates Ltd.

(57) ABSTRACT

The present disclosure herein relates to a biosignal detecting device and a biosignal detecting system including the same. According to an embodiment of the inventive concept, the biosignal detecting device is built in a vehicle seat. The biosignal detecting device includes an antenna block. The antenna block transmits a transmission signal to a person seated on the vehicle seat and receives a return signal corresponding to the transmission signal. The antenna block and one surface contacting the seated person are spaced apart from each other so that a distance therebetween is two times or more greater than a wavelength of the transmission signal. According to an embodiment of the inventive concept, through an optimized arrangement of the biosignal detecting device, the biosignal of the seated person may be exactly and effectively detected.

11 Claims, 16 Drawing Sheets

(51) Int. Cl.
*A61B 5/18* (2006.01)
*G08B 31/00* (2006.01)
*A61B 5/16* (2006.01)
*A61B 5/024* (2006.01)
*A61B 5/0205* (2006.01)

(56) References Cited

U.S. PATENT DOCUMENTS

| | | | |
|---|---|---|---|
| 7,196,629 B2 | 3/2007 | Ruoss et al. | |
| 8,251,447 B2 | 8/2012 | Fujita et al. | |
| 8,706,204 B2 | 4/2014 | Seo et al. | |
| 8,725,311 B1 * | 5/2014 | Breed | G08B 21/06 600/300 |
| 8,874,301 B1 | 10/2014 | Rao et al. | |
| 8,957,779 B2 | 2/2015 | Wu et al. | |
| 9,272,689 B2 | 3/2016 | Fung et al. | |
| 2002/0038947 A1 * | 4/2002 | Baba | B60R 21/01532 280/735 |
| 2005/0073424 A1 | 4/2005 | Ruoss et al. | |
| 2006/0283652 A1 * | 12/2006 | Yanai | G08B 21/06 180/272 |
| 2007/0217622 A1 * | 9/2007 | Takeuchi | H04W 16/18 381/86 |
| 2010/0117411 A1 * | 5/2010 | Fujita | A61B 5/0205 297/217.1 |
| 2010/0137702 A1 | 6/2010 | Park et al. | |
| 2010/0222687 A1 | 9/2010 | Thijs et al. | |
| 2012/0169503 A1 * | 7/2012 | Wu | G08B 21/06 340/575 |
| 2013/0150741 A1 | 6/2013 | Noh et al. | |
| 2013/0207676 A1 * | 8/2013 | Virnich | B60N 2/002 324/684 |
| 2014/0024917 A1 * | 1/2014 | McMahon | A61B 5/4836 600/407 |
| 2014/0039330 A1 * | 2/2014 | Seo | A61B 5/0452 600/509 |
| 2014/0303899 A1 | 10/2014 | Fung et al. | |
| 2016/0025788 A1 * | 1/2016 | Fujita | G01R 29/105 343/703 |
| 2016/0354026 A1 * | 12/2016 | Zohar | B60N 2/976 |
| 2016/0354027 A1 * | 12/2016 | Benson | A61M 21/02 |
| 2016/0378112 A1 | 12/2016 | Ljubuncic et al. | |
| 2017/0332979 A1 * | 11/2017 | Nagisetty | A61B 5/7282 |
| 2019/0039623 A1 * | 2/2019 | Kim | B60W 40/08 |

\* cited by examiner

BIOSIGNAL DETECTING DEVICE AND BIOSIGNAL DETECTING SYSTEM
INCLUDING THE SAME

CROSS-REFERENCE TO RELATED APPLICATIONS

This U.S. non-provisional patent application claims priority under 35 U.S.C. § 119 of Korean Patent Application No. 10-2017-0098258, filed on Aug. 2, 2017, the entire contents of which are hereby incorporated by reference.

BACKGROUND

The present disclosure herein relates to a biosignal detection of a vehicle passenger, and more particularly, to a biosignal detecting device built in a vehicle seat and a biosignal detecting system including the same.

Various electronic devices are provided in a vehicle to secure convenience of a user using the vehicle. In particular, devices for recognizing a health condition of a driver by measuring a biosignal of a vehicle driver or the like are provided in a vehicle. Such devices are mainly provided for inducing a safe driving of the driver and preventing accidents. Accordingly, various researches and developments on a method for effectively detecting a biosignal of a vehicle driver are being performed. Also, various researches and developments on a measure for effectively utilizing the detected biosignal are being performed.

Furthermore, in recent years, various devices for providing a pleasant and comfortable driving environment to passengers including the driver are provided in a vehicle. For example, vehicle seats including a seat fan or a heating wire for providing a temperature suitable to the passengers are provided. Since various devices for convenience are provided in a limited space of recent vehicles, a measure for implementing a unique function without disturbing a function of each of the devices for convenience.

SUMMARY

The present disclosure provides a biosignal detecting device built in a vehicle seat to exactly and effectively detect a biosignal and provide a safe driving environment by using the detected biosignal and a biosignal detecting system including the same.

An embodiment of the inventive concept provides a biosignal detecting device that is built in a vehicle seat. The biosignal detecting device includes an antenna block configured to transmit a transmission signal to a person seated on the vehicle seat and receive a return signal corresponding to the transmission signal. One surface, which contacts the seated person, of the vehicle seat and the antenna block are spaced apart from each other so that a distance therebetween is at least two times or more greater than a wavelength of the transmission signal.

In an embodiment, the biosignal detecting device may further include: an oscillator and a mixer. The oscillator may generate a local signal having the same frequency as that of the transmission signal. The mixer may mix the local signal with a detected signal generated on the basis of the return signal. The biosignal detecting device may generate a biosignal on the basis of a phase difference between the transmission signal and the return signal.

In an embodiment, the antenna block may be disposed adjacent to a wave absorber that is disposed to absorb a transmission signal transmitted to a seat face including a rotating blade. The antenna block may contact a separation member provided between the one surface and the antenna block and is spaced apart from the one surface so that a distance therebetween is two times or more greater than a wavelength of the transmission signal. Also, the antenna block may contact one surface of the vehicle seat having a groove. The groove may have a depth that is two times or more greater than a wavelength of the transmission signal.

In an embodiment of the inventive concept, a biosignal detecting system includes first to fourth antenna blocks and first and second signal transmitting/receiving part. The first and second antennal blocks may be built in the first vehicle seat. The third and fourth antenna blocks may be built in a second vehicle seat disposed at a side of the first vehicle seat. The first antenna block may transmit a first transmission signal toward a person seated on the first vehicle seat and receive a first return signal corresponding to the first transmission signal. The second antenna block may transmit a second transmission signal toward a rear seat disposed behind the first vehicle seat and receive a second return signal corresponding to the second transmission signal. The third antenna block may transmit a third transmission signal toward a person seated on the second vehicle seat and receive a third return signal corresponding to the third transmission signal. The fourth antenna block may transmit a fourth transmission signal toward the rear seat and receive a fourth return signal corresponding to the fourth transmission signal.

The first signal transmitting/receiving unit may generate a first biosignal on the basis of the first transmission signal and the first return signal. The first signal transmitting/receiving unit may generate a second biosignal on the basis of the second transmission signal and the second return signal. The second signal transmitting/receiving unit may generate a third biosignal on the basis of the third transmission signal and the third return signal. The second signal transmitting/receiving unit may generate a fourth biosignal on the basis of the fourth transmission signal and the fourth return signal. The second antenna block may further transmit a fifth transmission signal in a rear direction of the first vehicle seat. The fourth antenna block may further receive a fifth return signal corresponding to the fifth transmission signal. The second signal transmitting/receiving unit may generate a fifth biosignal of a person seated on an intermediate portion of the rear seat on the basis of the fifth transmission signal and the fifth return signal.

The biosignal detecting system may further include a drowsiness determining part, a seat occupancy determining part, and a communication module. The drowsiness determining unit may determine whether the seated person is drowsy on the basis of at least one of the first to fifth biosignals. The seat occupancy determining unit may determine whether the seated person is present on the basis of the first to fifth biosignals. The communication module may generate a biosignal of a passenger on the basis of the first to fifth biosignals and transmit the generated biosignal of the passenger to the outside through a wireless communication.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Hereinafter, embodiments of the inventive concept are exactly and precisely described so that the present disclosure may be easily implemented by those with ordinary skill in the technical field of the present invention. Hereinafter, a position relationship between components according to an embodiment of the inventive concept will be described. On the basis of a vehicle seat and a person seated on the vehicle seat, an upper portion, an upper end, or an upper side represents a direction from the ground to the seated person. A lower portion, a lower end, or a lower side represents a direction from the seated person to the ground. A front direction represents a direction from a backrest to the seated person. A rear direction represents a direction from the seated person to the backrest. Left and right sides are divided on the basis of a direction in which the person seated on the vehicle seat is viewed from the front.

Figure 1:
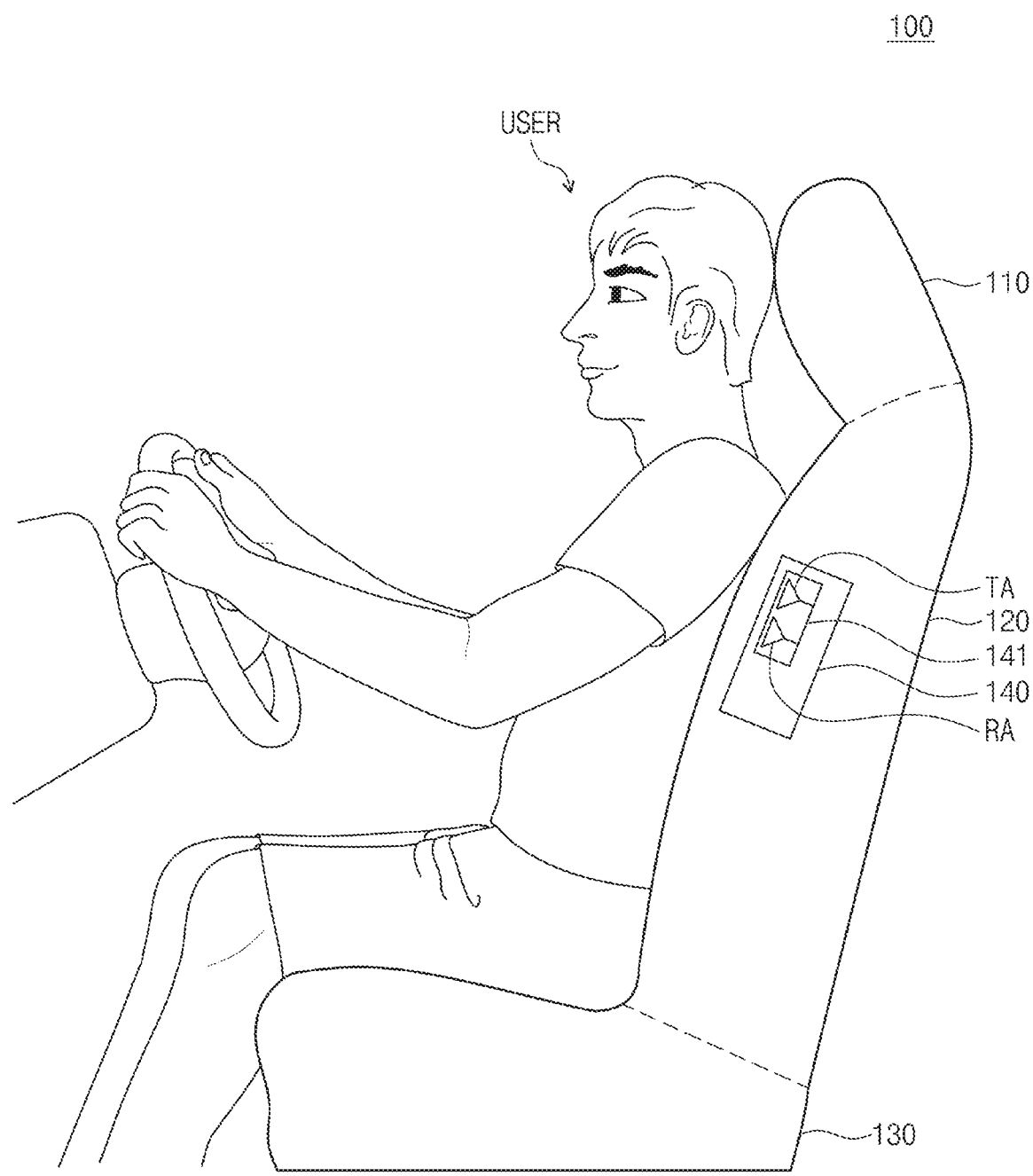
FIG. 1 is a view of a vehicle seat according to an embodiment of the inventive concept.

FIG. 1 is a view illustrating a vehicle seat according to an embodiment of the inventive concept. Referring to FIG. 1, a vehicle seat 100 includes a head support part 110, a backrest part 120, a bottom part 130, and a biosignal detecting device 140. The vehicle seat 100 may include all of a driver seat, a front passenger seat, and a rear seat in a vehicle. Also, according an embodiment of the inventive concept, an object may include an animal boarding on the vehicle seat 100 as well as a seated person USER.

The head support part 110 is disposed on an upper end of the backrest part 120 to support a head of the seated person USER. The backrest part 120 may be disposed on a rear upper end of the bottom part 130 so that the seated person USER is able to lean one's back against the backrest part 120. The bottom part 130 is configured so that the seated person USER is able to seat thereon. Although the head support part 110, the backrest part 120, and the bottom part 130 are integrated with each other as an example in FIG. 1, these components may be separated. For example, each of the head support part 110, the backrest part 120, and the bottom part 130 may have various shapes.

The biosignal detecting device 140 may be disposed in the backrest part 120. The biosignal detecting device 140 may be built in the backrest part 120. The biosignal detecting device 140 may measure breath and heartbeat of the seated person USER. A portion of the biosignal detecting device 140 is disposed in the backrest part 120 that is adjacent to a chest of the seated person USER to easily measure the breath and heartbeat of the seated person USER. Since the biosignal detecting device 140 detects a signal at a back portion of the seated person USER, the signal is not disturbed by motion of an arm or a shoulder of the seated person USER.

The biosignal detecting device 140 includes an antenna block 141. The antenna block 141 is disposed in the backrest part 120 to exactly detect a biosignal. Although the biosignal detecting device 140 is built in the backrest part 120 in FIG. 1, other components except for the antenna block 141 may not be built in the backrest part 120. For example, the other components except for the antenna block 141 may be disposed in the bottom part 130 or disposed at the outside. The antenna block 141 may not contact the seated person USER. The antenna block 141 is spaced more than a predetermined distance from the seated person USER. Here, the predetermined distance may be a distance that is satisfied with a far-field condition in which a signal emitted from the antenna block 141 is approximated to a plane wave.

Although the antenna block 141 may include a transmission antenna TA and a receiving antenna RA, an embodiment of the inventive concept is not limited thereto. For example, the antenna block 141 may include a single antenna performing functions of the transmission antenna TA and the receiving antenna RA. The transmission antenna TA may transmit a transmission signal to the seated person USER. The transmission signal is reflected by the seated person USER. The receiving antenna RA may receive a return signal reflected by the seated person USER.

The biosignal detecting device 140 may detect the motion of the seated person USER by using the return signal. For example, the biosignal detecting device 140 may measure a Doppler frequency by using the transmission signal and the return signal. The biosignal detecting device 140 may detect precise motion such as heartbeat by using the measured Doppler frequency. That is, the biosignal detecting device 140 may use the Doppler frequency to generate a biosignal such as heartbeat or breath.

For another example, the biosignal detecting device 140 may detect the motion of the seated person USER by measuring an arrival time of the return signal. To this end, the biosignal detecting device 140 may transmit an impulse as the transmission signal. In this case, the biosignal detecting device 140 may detect relatively large motion such as breath. That is, the biosignal detecting device 140 may generate the biosignal such as the breath by using a transmitting and receiving time of the signal.

Figure 2:
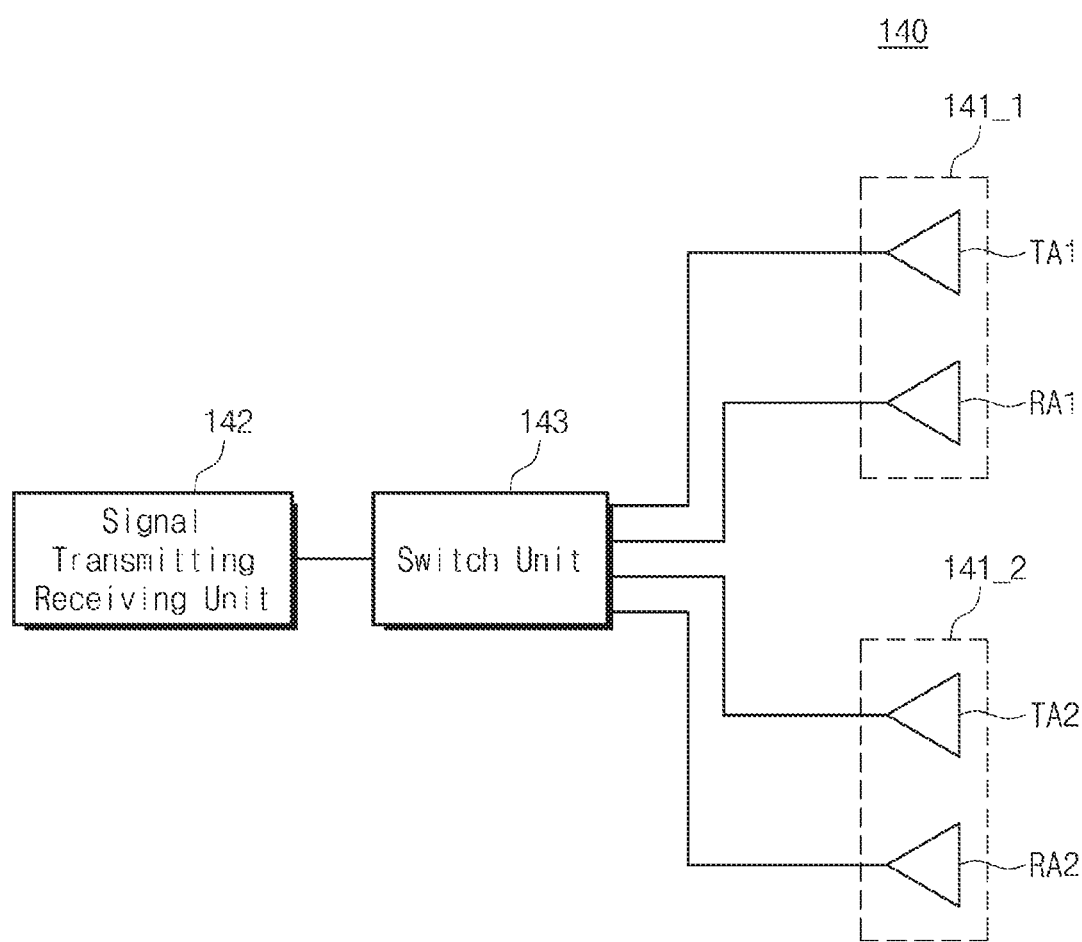
FIGS. 2 and 3 are block diagrams of a biosignal detecting device according to an embodiment of the inventive concept.

FIG. 2 is a block diagram of the biosignal detecting device according to an embodiment of the inventive concept. The biosignal detecting device in FIG. 1 is described in detail in a biosignal detecting device 140 in FIG. 2. Referring to FIG. 2, the biosignal detecting device 140 may include a first antenna block 141_1, a second antenna block 141_2, a signal transmitting/receiving unit 142, and a switch unit 143. Although two antenna blocks are exemplarily illustrated in FIG. 2, an embodiment of the inventive concept is not limited thereto. For example, the various numbers of the antenna blocks may be provided. Also, like FIG. 1, the biosignal detecting device 140 may include one antenna block. In this case, the switch unit 143 may not be provided.

The first antenna block 141_1 may include a first transmission antenna TA1 and a first receiving antenna RA1. The first transmission antenna TA1 may transmit a first transmission signal. The first receiving antenna RA1 may receive a first return signal that is a reflected first transmission signal. The second antenna block 141_2 may include a second transmission antenna TA2 and a second receiving antenna RA2. The second transmission antenna TA2 may transmit a second transmission signal. The second receiving antenna RA2 may receive a second return signal that is a reflected second transmission signal. That is, the first and second antenna blocks 141_1 and 141_2 may perform the same function as that of the antenna block 141 in FIG. 1.

The first and second antenna blocks 141_1 and 141_2 may provide a transmission signal to the same seated person. When the antenna block is provided in plurality, a more wide range of biosignal of the seated person may be detected. Accordingly, degradation in accuracy of biosignal measurement may be prevented, which is caused by a posture of the seated person. Also, the first and second antenna blocks 141_1 and 141_2 may provide a transmission signal to different seated persons. For example, the first antenna block 141_1 may transmit a first transmission signal to a person seated on a vehicle seat including the biosignal detecting device 140, and the second antenna block 141_2 may transmit a second transmission signal to a person seated on a rear seat. Contents regarding this will be described in detail below with reference to FIG. 10.

The signal transmitting/receiving unit 142 may provide the first transmission signal to the first antenna block 141_1 or the second transmission signal to the second antenna block 141_2. Also, the signal transmitting/receiving unit 142 may receive the first return signal from the first antenna block 141_1 or the second return signal from the second antenna block 141_2. The signal transmitting/receiving unit 142 may detect the motion of the seated person by using the first return signal and generate a first biosignal. The signal transmitting/receiving unit 142 may detect the motion of the seated person by using the second return signal and generate a second biosignal.

The switch unit 143 may determine an electric connection relationship between the signal transmitting/receiving unit 142 and the first antenna block 141_1 and between the signal transmitting/receiving unit 142 and the second antenna block 141_2. The switch unit 143 may selectively connect the signal transmitting/receiving unit 142 to one of the first and second antenna blocks 141_1 and 141_2. When the signal transmitting/receiving unit 142 is connected to the first antenna block 141_1, the switch unit 143 may deliver the first transmission signal to the first antenna block 141_1 and the first return signal to the signal transmitting/receiving unit 142. When the signal transmitting/receiving unit 142 is connected to the second antenna block 141_2, the switch unit 143 may deliver the second transmission signal to the second antenna block 141_2 and the second return signal to the signal transmitting/receiving unit 142.

Figure 3:
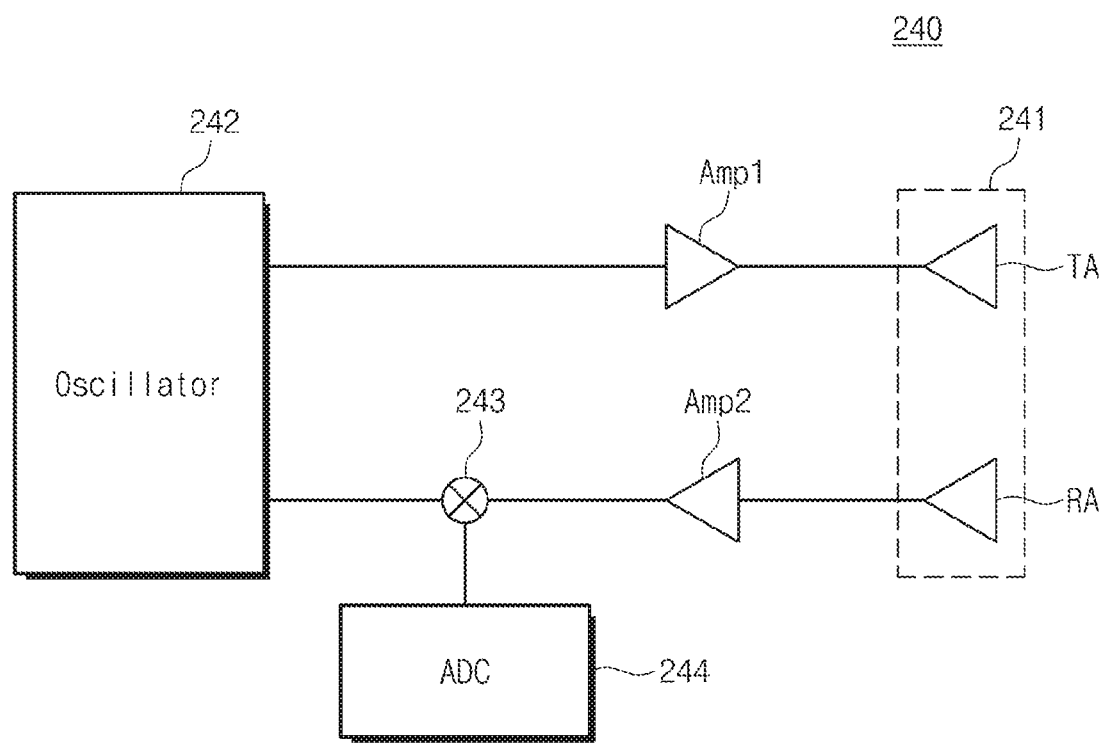

FIG. 3 is a block diagram of the biosignal detecting device according to an embodiment of the inventive concept. FIG. 3 is a view for explaining a process of generating a biosignal by using a transmission signal and a return signal in detail. Referring to FIG. 3, a biosignal detecting device 240 includes an antenna block 241, a first amplifier Amp1, a second amplifier Amp2, an oscillator 242, a mixer 243, and an analog-digital converter 244. The antenna block 241 may include a transmission antenna TA and a receiving antenna RA, The first amplifier Amp1, the second amplifier Amp2, the oscillator 242, the mixer 243, and the analog-digital converter 244 may be components provided in the signal transmitting/receiving unit 142 in FIG. 2.

The oscillator 242 generates a local signal. The local signal may have a specific transmission frequency. The local signal may be a sinusoidal signal. The oscillator 242 may provide the local signal to the first amplifier Amp1. The first amplifier Amp1 may amplify the local signal. The transmission signal that is the amplified local signal may be delivered to the transmission antenna TA. The transmission antenna TA may emit the transmission signal to the outside. The receiving antenna RA may receive a return signal corresponding to the transmission signal. The receiving antenna RA may provide the return signal to the second amplifier Amp2. The second amplifier Amp2 may amplify the return signal. The detected signal that is the amplified return signal is provided to the mixer 243.

The mixer 243 receives a detected signal generated on the basis of the return signal. Also, the mixer 243 receives the local signal from the oscillator 242. The mixer 243 mixes the local signal with the detected signal. On the basis of the Doppler effect, an element of the transmission signal and an element of the return signal may be varied. In detail, a phase difference between the transmission signal and the return signal may be present. A signal in which the local signal and the detected signal are mixed may represent an element variation of the return signal. The mixed signal is provided to the analog-digital converter 244.

The analog-digital converter 244 converts the mixed analog signal into a digital signal. The biosignal detecting device 240 may further include a signal processing device (not shown) generating a biosignal on the basis of the converted digital signal. The digital signal may include an element corresponding to the motion of the seated person. For example, the digital signal may include a heartbeat element corresponding to motion of a heart or a breath element corresponding to motion of a lung. For example, the signal processing device (not shown) may filter the digital signal to separate the heartbeat element from the breath element and generate the biosignal on the basis of the heartbeat element or the breath element.

FIGS. 4A to 4D are plan views of a vehicle seat illustrating an arrangement of an antenna block according to an embodiment of the inventive concept. FIGS. 4A to 4D are views illustrating a contact surface at which the backrest part of the vehicle seat and the seated person contact each other. The antenna blocks may be disposed inside the backrest part. In this case, the antenna blocks may not be exposed on the contact surface. That is, the antenna blocks in FIGS. 4A to 4D are illustrated by a solid line for convenience of description. Also, in the drawings below, components disposed inside the backrest part are illustrated by a solid line for the same reason.

Figure 4A:
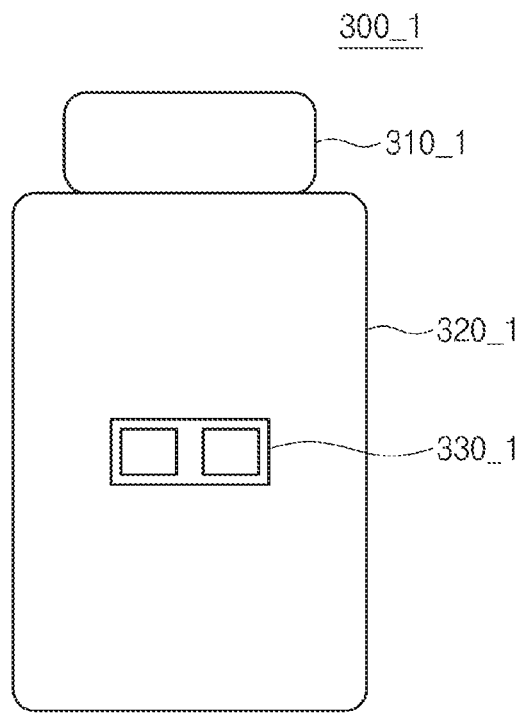
FIGS. 4A to 4D are front views of a vehicle seat illustrating an arrangement of an antenna block according to an embodiment of the inventive concept.

Referring to FIG. 4A, a vehicle seat 300_1 includes a head support part 310_1, a backrest part 320_1, and an antenna block 330_1. Like FIG. 4A, one antenna block 330_1 may be provided in the vehicle seat 300_1. The antenna block 330_1 may be built in the backrest part 320_1. The antenna block 330_1 may be disposed adjacent to a chest to easily detect motion of a heart or a lung of the seated person.

Figure 4B:
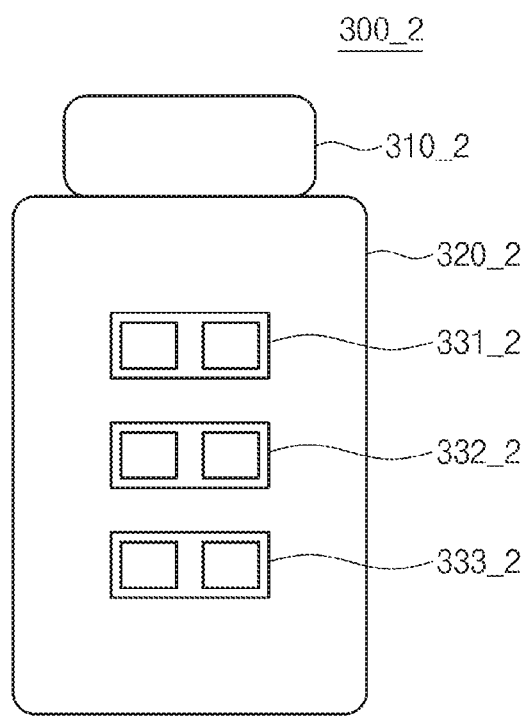

Referring to FIG. 4B, a vehicle seat 300_2 may include a head support part 310_2, a backrest part 320_2, and first to third antenna blocks 331_2, 332_2, and 333_2. Although it is illustrated that the vehicle seat 300_2 includes three antenna blocks, an embodiment of the inventive concept is not limited to the number of the antenna blocks. The first to third antenna blocks 331_2, 332_2, and 333_2 may be built in the backrest part 320_2. The first to third antenna blocks 331_2, 332_2, and 333_2 may be arranged in a row in a longitudinal direction. The first to third antenna blocks 331_2, 332_2, and 333_2 may alternatively provide a transmission signal and alternatively receive a return signal. In comparison with FIG. 4A, since the vehicle seat 300_2 may detect a wide range of motion, an exact and stable biosignal may be generated.

Figure 4C:
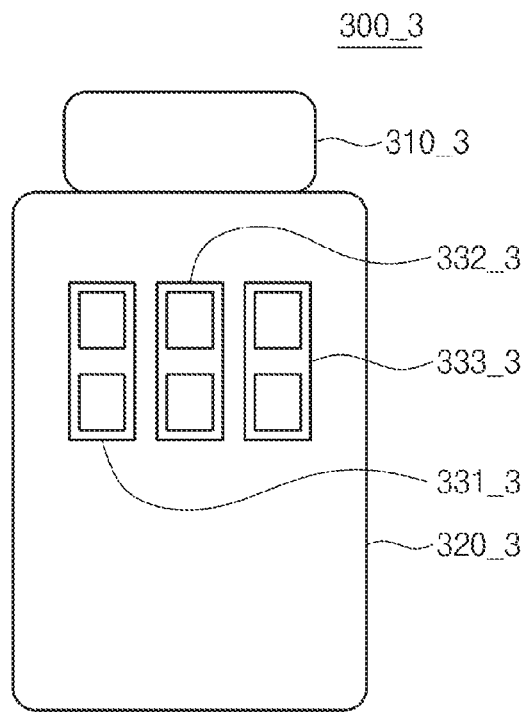

Referring to FIG. 4C, a vehicle seat 300_3 may include a head support part 310_3, a backrest part 320_3, and first to third antenna blocks 331_3, 332_3, and 333_3. Although it is illustrated that the vehicle seat 300_3 includes three antenna blocks, an embodiment of the inventive concept is not limited to the number of the antenna blocks. The first to third antenna blocks 331_3, 332_3, and 333_3 may be built in the backrest part 320_3. The first to third antenna blocks 331_3, 332_3, and 333_3 may be arranged in a row in a transverse direction. In comparison with the vehicle seat 300_1 in FIG. 4A, since the vehicle seat 300_3 may detect a wide range of motion, an exact and stable biosignal may be generated.

Figure 4D:
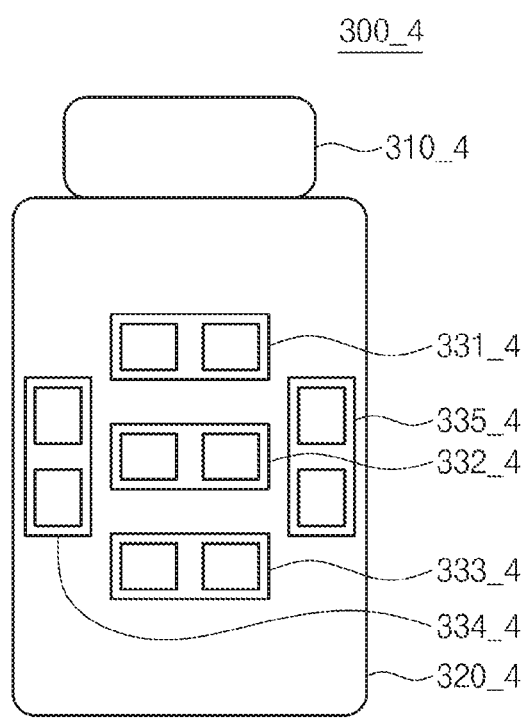

Referring to FIG. 4D, a vehicle seat 300_4 may include a head support part 310_4, a backrest part 320_4, and first to fifth antenna blocks 331_4 to 335_4. Although it is illustrated that the vehicle seat 300_4 includes five antenna blocks, an embodiment of the inventive concept is not limited to the number of the antenna blocks. The first to third antenna blocks 331_4, 332_4, and 333_4 may be arranged in a row in a longitudinal direction. The fourth antenna block 334_4 may be disposed at a left side of the first to third antenna blocks 331_4, 332_4, and 333_4, and the fifth antenna block 335_5 may be disposed at a right side of the first to third antenna blocks 331_4, 332_4, and 333_4. In comparison with FIGS. 4A to 4C, since the vehicle seat 300_4 may detect a more wide range of motion, an exact and stable biosignal may be generated.

Each of the antenna blocks in FIGS. 4A to 4D may include a transmission antenna and a receiving antenna. Also, the transmission antenna and the receiving antenna may be arranged in the transverse direction or the longitudinal direction. The arrangement of the transmission antenna and the receiving antenna may be arranged in various directions unlike FIGS. 4A to 4D. Also, the antenna blocks in FIGS. 4A to 4D are exemplarily arranged. For example, the antenna blocks may be arranged in X-shaped directions or in a two-dimensional array having a plurality of rows and columns.

FIGS. 5A to 5D are front views of a vehicle seat illustrating an arrangement of an antenna block and a seat fan according to an embodiment of the inventive concept. FIGS. 5A to 5D are views exemplarily illustrating the arrangement of the antenna blocks when the vehicle seat further include a movable component. The biosignal detecting device according to an embodiment of the inventive concept detects the motion of the seated person to generate the biosignal. When a transmission signal is provided to the movable element, a return signal may include an element corresponding to the motion of an inner component as well as an element corresponding to the motion of the heart and the lung Referring to FIG. 5A, a vehicle seat 400_1 includes a head support part 410_1, a backrest part 420_1, an antenna block 430_1, a seat fan 440_1, and a wave absorber 450_1. The antenna block 430_1, the seat fan 440_1, and the wave absorber 450_1 may be built in the backrest part 420_1. The seat fan 440_1 may include a rotating blade. The seat fan 440_1 may further include a motor for rotating the rotating blade. The seat fan 440_1 may circulate air by using the rotating blade. The vehicle seat 400_1 may provide a comfortable vehicle environment to the seated person by using the seat fan 440_1. The person seated on the vehicle seat 400_1 for a long time may generate sweat, and the seat fan 440_1 may lower a body temperature of the seated person or remove moisture caused by the sweat.

The wave absorber 450_1 is disposed between the antenna block 430_1 and the seat fan 440_1. The antenna block 430_1 emits a transmission signal to detect the motion of the seated person. However, the rotating blade of the seat fan 440_1 may rotate. The transmission signal may be reflected by the seat fan 440_1 and carried to the antenna block 430_1. In this case, the antenna block 430_1 may detect the motion of the rotating blade as well as the motion of the seated person. The wave absorber 450_1 blocks the transmission signal from being reached to the seat fan 440_1. The wave absorber 450_1 may absorb the transmission signal traveling in a direction toward the seat fan 440_1. Accordingly, the return signal provided to the antenna block 430_1 may not include a noise element generated by the seat fan 440_1.

Figure 5A:
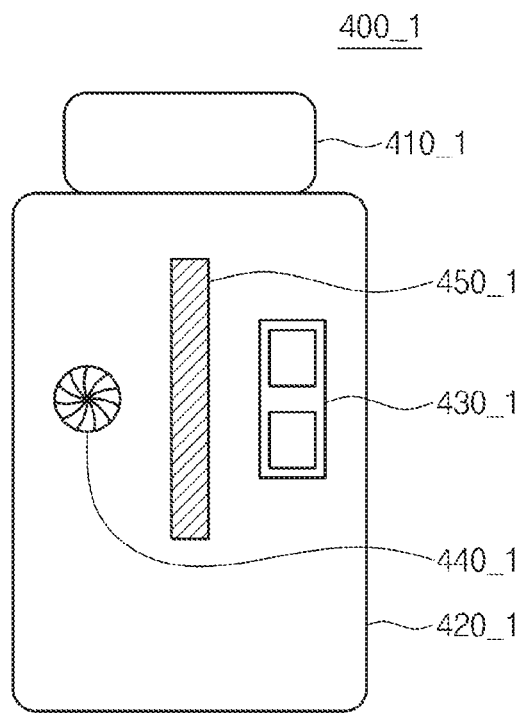
FIGS. 5A to 5D are front views of a vehicle seat illustrating an arrangement of an antenna block and a seat fan according to an embodiment of the inventive concept.
Figure 5B:
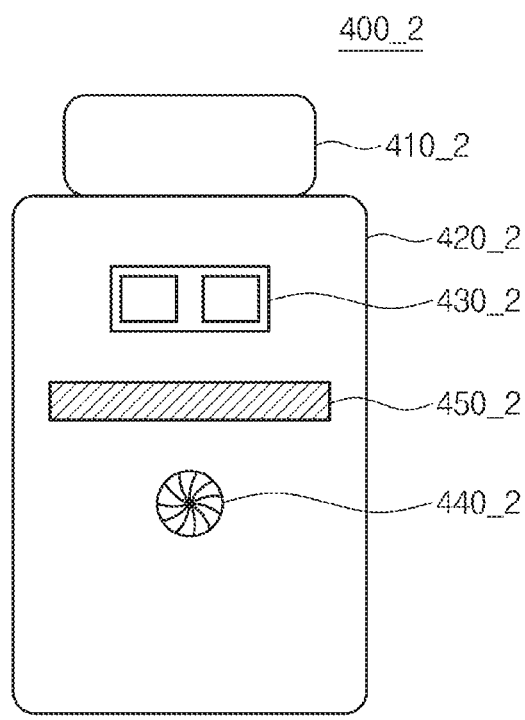

Referring to FIG. 5B, a vehicle seat 400_2 includes a head support part 410_2, a backrest part 420_2, an antenna block 430_2, a seat fan 440_2, and a wave absorber 450_2. Like the vehicle seat 400_1 in FIG. 5A, the antenna block 430_2, the wave absorber 450_2, and the seat fan 440_2 may be sequentially arranged in the transverse direction. Alternatively, like the vehicle seat 400_2 in FIG. 5B, the antenna block 430_2, the wave absorber 450_2, and the seat fan 440_2 may be sequentially arranged in the longitudinal direction. However, an embodiment of the inventive concept is not limited to those in FIGS. 5A and 5B. For example, the wave absorber may separate the antenna block from the seat fan.

Figure 5C:
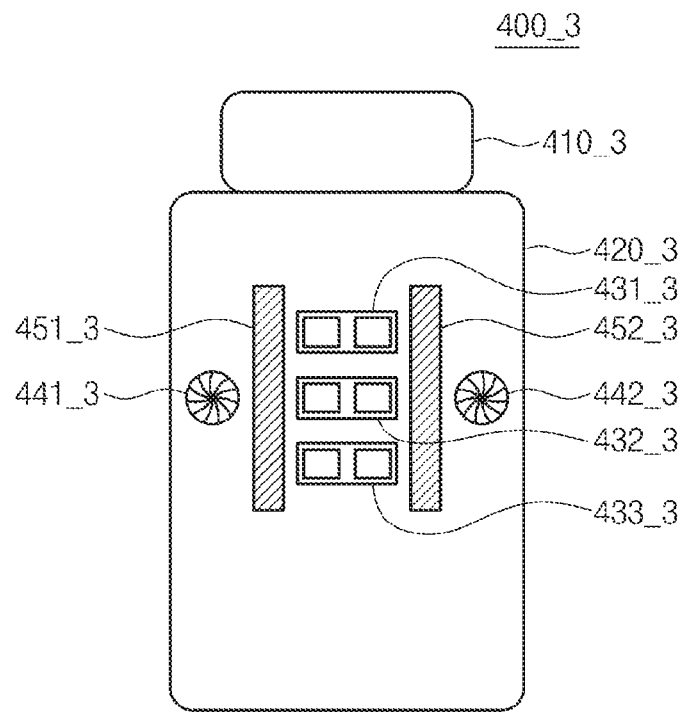

Referring to FIG. 5C, a vehicle seat 400_3 may include a head support part 410_3, a backrest part 420_3, first to third antenna blocks 431_3, 432_3, and 433_3, first and second seat fans 441_3 and 442_3, and first and second wave absorber 451_3 and 452_3. A component arrangement when the vehicle seat 400_3 includes a plurality of antenna blocks is exemplarily illustrated in FIG. 5C in comparison with FIGS. 5A and 5B. The first to third antenna blocks 431_3, 432_3, and 433_3 may be arranged in a row in the transverse direction.

The first seat fan 441_3 may be disposed at a left side of the first to third antenna blocks 431_3, 432_3, and 433_3. The second seat fan 442_3 may be disposed at a right side of the first to third antenna blocks 431_3, 432_3, and 433_3. The first wave absorber 451_3 is disposed between the first seat fan 441_3 and the first to third antenna blocks 431_3, 432_3, and 433_3. The first wave absorber 451_3 prevents the transmission signal generated by the first to third antenna blocks 431_3, 432_3, and 433_3 from being reached to the first seat fan 441_3. The second wave absorber 452_3 is disposed between the second seat fan 442_3 and the first to third antenna blocks 431_3, 432_3, and 433_3. The second wave absorber 452_3 prevents the transmission signal generated by the first to third antenna blocks 431_3, 432_3, and 433_3 from being reached to the second seat fan 442_3.

Figure 5D:
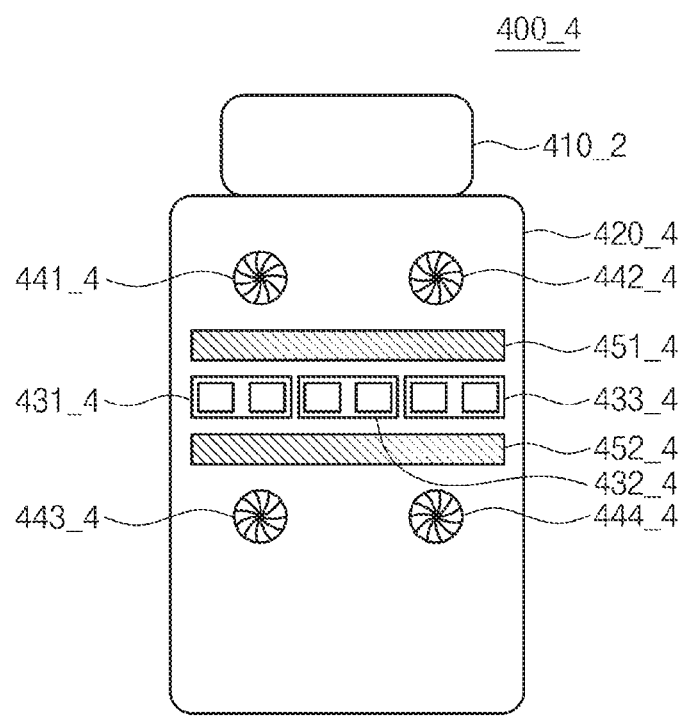

Referring to FIG. 5D, a vehicle seat 400_4 may include a head support part 410_4, a backrest part 420_4, first to third antenna blocks 431_4, 432_4, and 433_4, first to fourth seat fans 441_4 to 444_4, and first and second wave absorbers 451_4 and 452_4. The first to third antenna blocks 431_4, 432_4, and 433_4 may be arranged in a row in the transverse direction. The first and second seat fans 441_4 and 442_4 may be disposed above the first to third antenna blocks 431_4, 432_4, and 433_4. The third and fourth seat fans 443_4 and 444_4 may be disposed below the first to third antenna blocks 431_4, 432_4, and 433_4.

The first wave absorber 451_4 is disposed between the first and second seat fans 441_4 and 442_4 and the first to third antenna blocks 431_4, 432_4, and 433_4. The first wave absorber 451_3 prevents the transmission signal generated by the first to third antenna blocks 431_4, 432_4, and 433_4 from being reached to the first and second seat fans 441_4 and 442_4. The second wave absorber 452_4 is disposed between the third and fourth seat fans 443_4 and 444_4 and the first to third antenna blocks 431_4, 432_4, and 433_4. The second wave absorber 452_3 prevents the transmission signal generated by the first to third antenna blocks 431_4, 432_4, and 433_4 from being reached to the third and fourth seat fans 443_4 and 444_4.

Referring to the vehicle seats 440_1 to 440_4 in FIGS. 5A to 5D, the seat fan and the antenna block is required to be separated. Also, the vehicle seats 440_1 to 440_4 is configured so that the seat fan is not disposed between the seated person and the antenna block to prevent the motion of the seat fan from being reflected to the return signal. Unlike FIGS. 5A to 5D, the seat fan, the wave absorber, and the antenna block may be variously arranged. Also, the vehicle seat may include a movable component in addition to the seat fan. The wave absorber may be disposed between the movable component and the antenna block.

Figure 6:
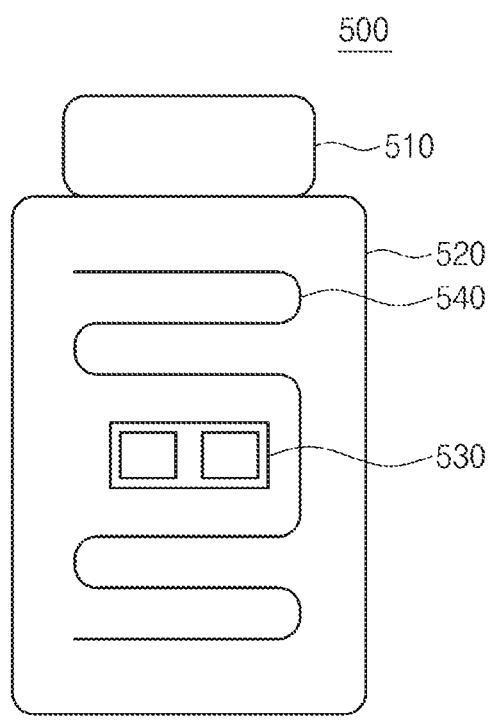
FIG. 6 is a front view of a vehicle seat illustrating an arrangement of an antenna block and a heating wire according to an embodiment of the inventive concept.

FIG. 6 is a front view of a vehicle seat illustrating an arrangement of an antenna block and a heating wire according to an embodiment of the inventive concept. FIG. 6 is a view exemplarily illustrating an arrangement of the antenna block when the vehicle seat 500 further includes a non-movable component. Referring to FIG. 6, the vehicle seat 500 includes a head support part 510, a backrest part 520, an antenna block 530, and a heating wire 540. The antenna block 530 and the heating wire 540 may be built in the backrest part 520. One or more antenna blocks 530 may be provided.

The heating wire 540 may generate heat to increase a temperature of the vehicle seat. The heating wire 540 may be provided over the entire backrest part to effectively increase the temperature of an entire contact surface, which contacts the seated person, of the backrest part 520. The antenna block 530 and the heating wire 540 are spaced apart from each other. Since the heating wire 540 is non-movable unlike the seat fan, an additional wave absorber is not required. However, the heating wire 540 is not disposed between the seated person and the antenna block 530 to improve a transmitting/receiving efficiency of the antenna block 530. For example, the heating wire 540 may detour the antenna block 530.

Figure 7A:
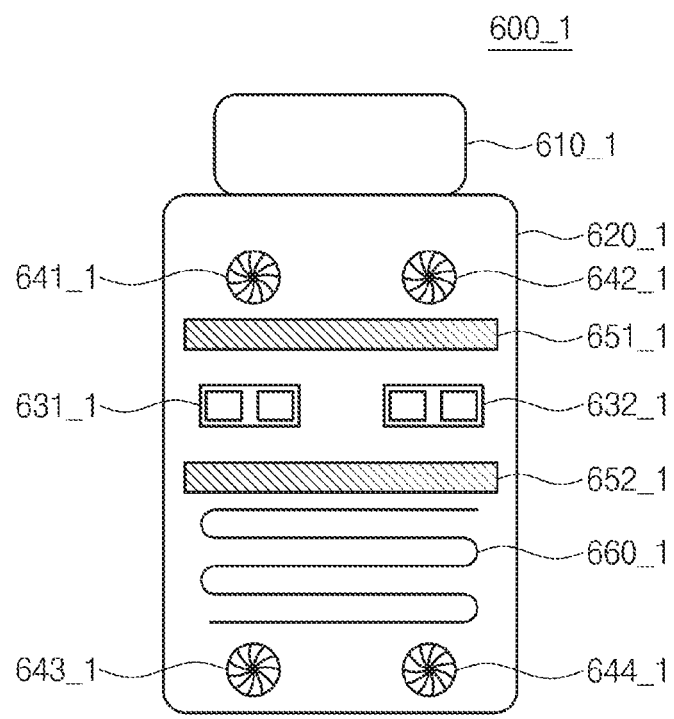
FIGS. 7A and 7B are front views of a vehicle seat illustrating an arrangement of an antenna block, a seat fan, and a heating wire according to another embodiment of the inventive concept.
Figure 7B:
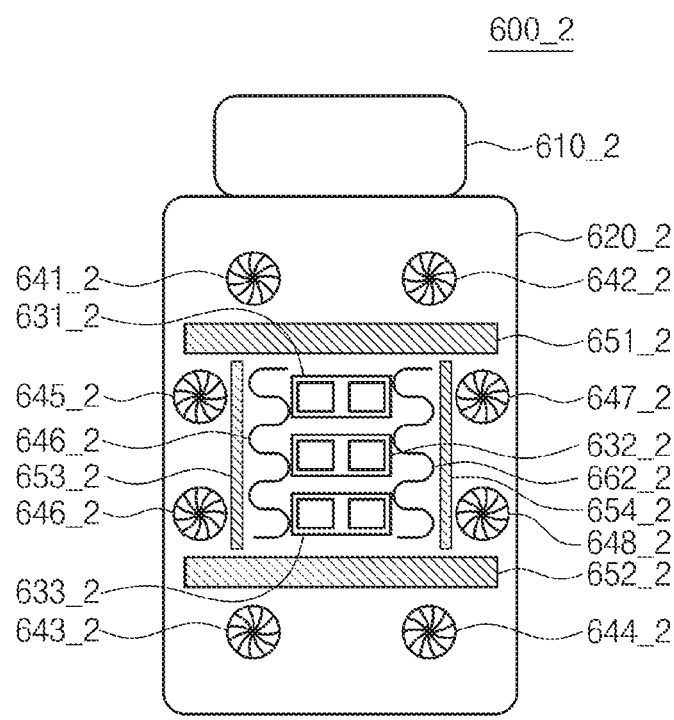

FIGS. 7A and 7B are front views of a vehicle seat illustrating an arrangement of an antenna block, a seat fan, and a heating wire according to an embodiment of the inventive concept. FIGS. 7A and 7B are views exemplarily illustrating an arrangement of vehicle seats 600_1 and 600_2 in which various components are built in. The antenna block, the seat fan, and the heating wire, which are included in the vehicle seats 600_1 and 600_2 in FIGS. 7A and 7B, may be built in the backrest parts 620_1 and 620_2.

Referring to FIG. 7A, the vehicle seat 600_1 includes a head support part 610_1, a backrest part 620_1, first and second antenna blocks 631_1 and 632_1, first to fourth seat fans 641_1 to 644_1, first and second wave absorbers 651_1 and 652_1, and a heating wire 660_1. The first and second antenna blocks 631_1 and 632_1 may be arranged in the transverse direction. The first and second seat fans 641_1 and 642_1 may be disposed above the first and second antenna blocks 631_1 and 632_1. The third and fourth seat fans 643_1 and 644_1 may be disposed below the first and second antenna blocks 631_1 and 632_1.

The first wave absorber 651_1 may be disposed between the first and second antenna blocks 631_1 and 632_1 and the first and second seat fans 641_1 and 642_1. The first wave absorber 651_1 prevents the transmission signal generated by the first and second antenna blocks 631_1 and 632_1 from being reached to the first and second seat fans 641_1 and 642_1. The second wave absorber 652_1 may be disposed between the first and second antenna blocks 631_1 and 632_1 and the third and fourth seat fans 643_1 and 644_1. When a distance between the first and second antenna blocks 631_1 and 632_1 and the third and fourth seat fans 643_1 and 644_1 is far enough, the transmission signal transmitting toward the seated person may not travel to the third and fourth seat fans 643_1 and 644_1. In this case, the second wave absorber 652_1 may not be disposed.

The heating wire 660_1 may be disposed between the first and second antenna blocks 631_1 and 632_1 and the third and fourth seat fans 643_1 and 644_1. The heating wire 660_1 is spaced apart from the first and second antenna blocks 631_1 and 632_1. The heating wire 660_1 may perform a function for increasing a temperature of the vehicle seat 600_1.

Referring to FIG. 7B, a vehicle seat 600_2 may include a head support part 610_2, a backrest part 620_2, first to third antenna blocks 631_2, 632_2, and 633_2, first to eighth seat fans 641_2 to 648_2, and first to fourth wave absorbers 651_2 to 654_4. The first to third antenna blocks 631_2, 632_2, and 633_2 may be arranged in a longitudinal direction.

The first and second seat fans 641_2 and 642_2 may be disposed above the first to third antenna blocks 631_2, 632_2, and 633_2. The third and fourth seat fans 643_2 and 644_2 may be disposed below the first to third antenna blocks 631_2, 632_2, and 633_2. The fifth and sixth seat fans 645_2 and 646_2 may be disposed at a left side of the first to third antenna blocks 631_2, 632_2, and 633_2. The seventh and eighth seat fans 647_2 and 648_2 may be disposed at a right side of the first to third antenna blocks 631_2, 632_2, and 633_2.

The first wave absorber 651_2 may be disposed between the first to third antenna blocks 631_2, 632_2, and 633_2 and the first and second seat fans 641_2 and 642_2. The second wave absorber 652_2 may be disposed between the first to third antenna blocks 631_2, 632_2, and 633_2 and the third and fourth seat fans 643_2 and 644_2. The third wave absorber 653_2 may be disposed between the first to third antenna blocks 631_2, 632_2, and 633_2 and the fifth and sixth seat fans 645_2 and 646_2. The fourth wave absorber 654_2 may be disposed between the first to third antenna blocks 631_2, 632_2, and 633_2 and the seventh and eighth seat fans 647_2 and 648_2.

The first heating wire 661_2 may be disposed between the first to third antenna blocks 631_2, 632_2, and 633_2 and the fifth and sixth seat fans 645_2 and 646_2. The second heating wire 662_2 may be disposed between the first to third antenna blocks 631_2, 632_2, and 633_2 and the seventh and eighth seat fans 647_2 and 648_2.

Figure 8:
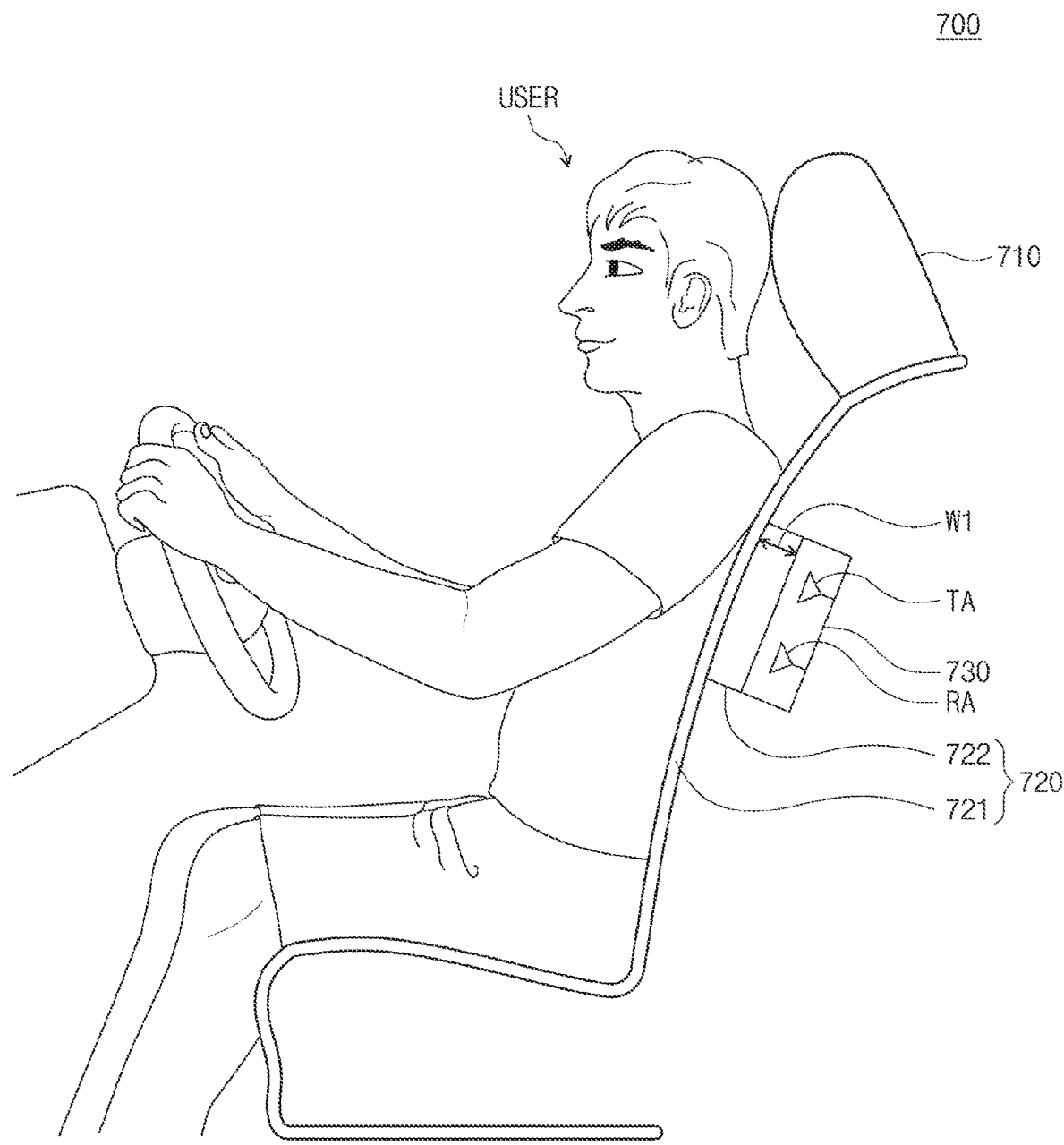
FIGS. 8 and 9 are side views of a vehicle seat according to an embodiment of the inventive concept.

FIG. 8 is a side view of a vehicle seat according to an embodiment of the inventive concept. Referring to FIG. 8, a vehicle seat 700 includes a head support part 710, a backrest part 720, and an antenna block 730. The antenna block 730 may include a transmission antenna TA and a receiving antenna RA, The head support part 710 and the antenna block 730 may be the head support part and the antenna block in FIGS. 1 to 7B.

The backrest part 720 may include a seat cover 721 and a separation member 722. The seat cover 721 surrounds the antenna block 730 and the separation member 722. The seat cover contacts the seated person USER. The seat cover 721 provides a surface of the backrest part 720 so that components built in the backrest part 720 do not directly contact the seated person USER. An embodiment of the inventive concept is not limited to a material of the seat cover 721. However, the seat cover disposed between the antenna block 730 and the seated person USER may not desirably include a metallic material to improve a signal transmitting/receiving efficiency between the antenna block 730 and the seated person USER.

The separation member 722 is disposed between the seat cover 721 and the antenna block 730. The separation member 722 may have one surface contacting the seat cover 721. The other surface, which faces the one surface, of the separation member 722 may contact the antenna block 730. The separation member 722 may fix the antenna block 730. The separation member 722 may not desirably include a metallic material to improve a signal transmitting/receiving efficiency between the antenna block 730 and the seated person USER. The separation member 722 may be made of a material having a dielectric constant of about 1, e.g., Styrofoam, plastic, or rubber.

The separation member 722 allows one surface, which contacts the seated person USER, of the backrest part 720 and the antenna block 730 to be spaced more than a predetermined distance. The separation member 722 may have a first thickness W1 so that a back portion of the seated person USER is disposed in a far-field region. For example, the transmission antenna TA of the antenna block 730 may provide a transmission signal having a transmission frequency to the seated person USER. The transmission frequency may be in a range from about 1 GHz to several tens GHz to detect a precise motion of a chest of the seated person USER. In this case, the transmission signal may have a wavelength of several mm to several tens cm. The first thickness W1 may have a length that is two times or more greater than the wavelength of the transmission signal so that the seated person USER is disposed in the far-field region. For example, when the transmission frequency is about 10 GHz, the first thickness W1 may be equal to or greater than about 6 cm. Alternatively, a sum of the first thickness W1 and the thickness of the seat cover 721 may be equal to or greater than about 6 cm.

Figure 9:
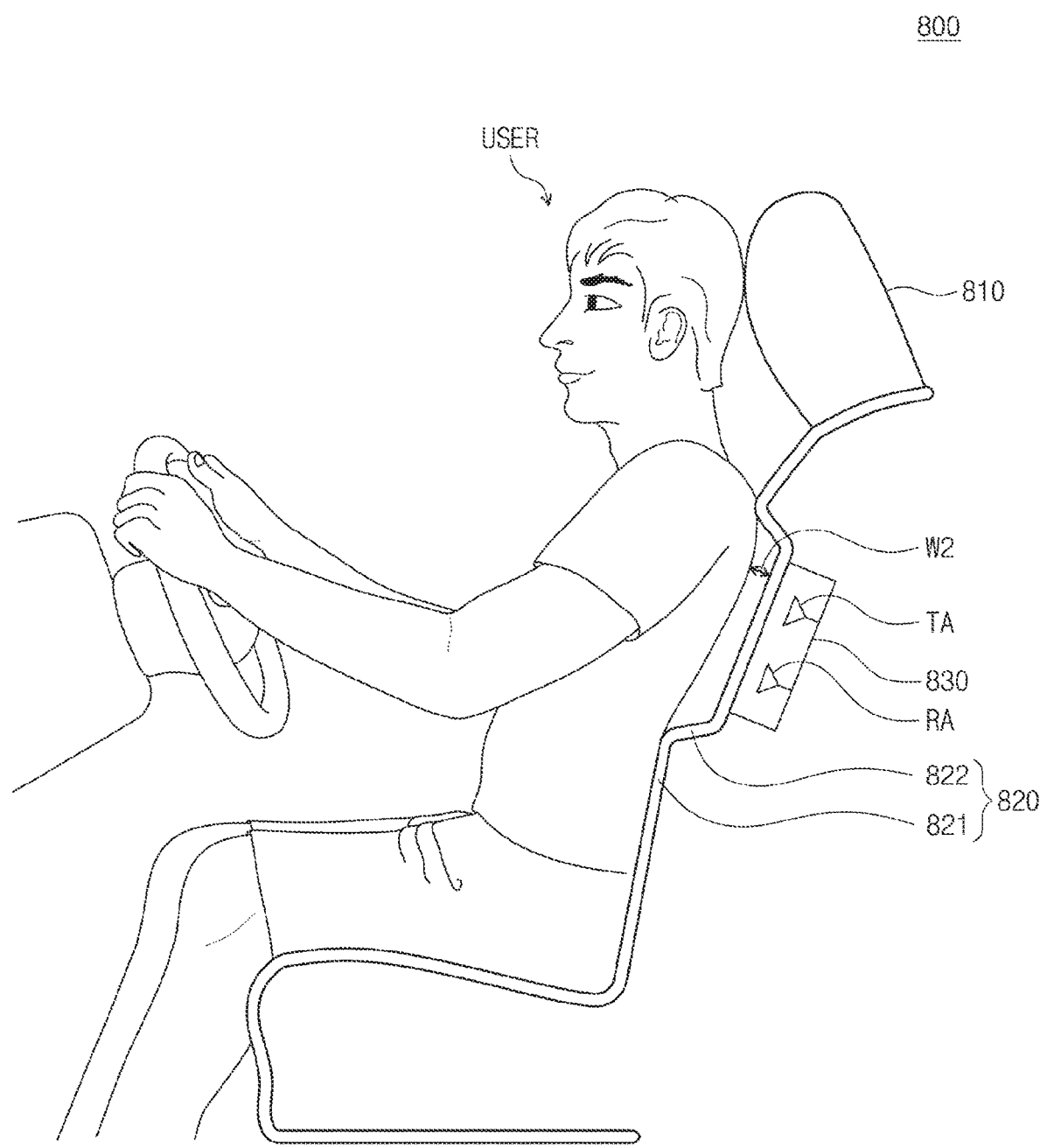

FIG. 9 is a side view of a vehicle seat according to an embodiment of the inventive concept. Referring to FIG. 9, a vehicle seat 800 includes a head support part 810, a backrest part 820, and an antenna block 830. The antenna block 830 may include a transmission antenna TA and a receiving antenna RA, The head support part 810 and the antenna block 830 may be the head support part and the antenna block in FIGS. 1 to 8.

The backrest part 820 may include a seat cover 821. The seat cover 821 surrounds the antenna block 830. Like FIG. 8, the seat cover 821 provides a surface of the backrest part 820. The seat cover 821 may have a recessed portion 822 contacting the antenna block 830. Although not shown, a protection film for protecting a surface of the antenna block 830 may be provided between the antenna block 830 and the recessed portion 822. Also, the recessed portion 822 may not desirably include a metallic material to improve a signal transmitting/receiving efficiency between the antenna block 830 and the seated person USER.

The recessed portion 822 may allow a portion of the vehicle seat 800 to be recessed in a rear direction of the seated person USER. The recessed portion 822 may provide a groove having a second thickness W2 between the seated person USER and the backrest part 820. Like the first thickness W1 in FIG. 8, the second thickness W2 may have a length two times or more greater than a wavelength of the transmission signal provided from the antenna block 830. Alternatively, a sum of the second thickness W2 and the thickness of the recessed portion 822 may have a length that is two times or more greater than the wavelength of the transmission signal. The recessed portion 822 allows the seated person USER to be spaced apart form the antenna block 830 so that the seated person USER is disposed in the far-field region. Accordingly, the transmission signal arrived to the seated person USER may be approximated to a plane wave.

Figure 10:
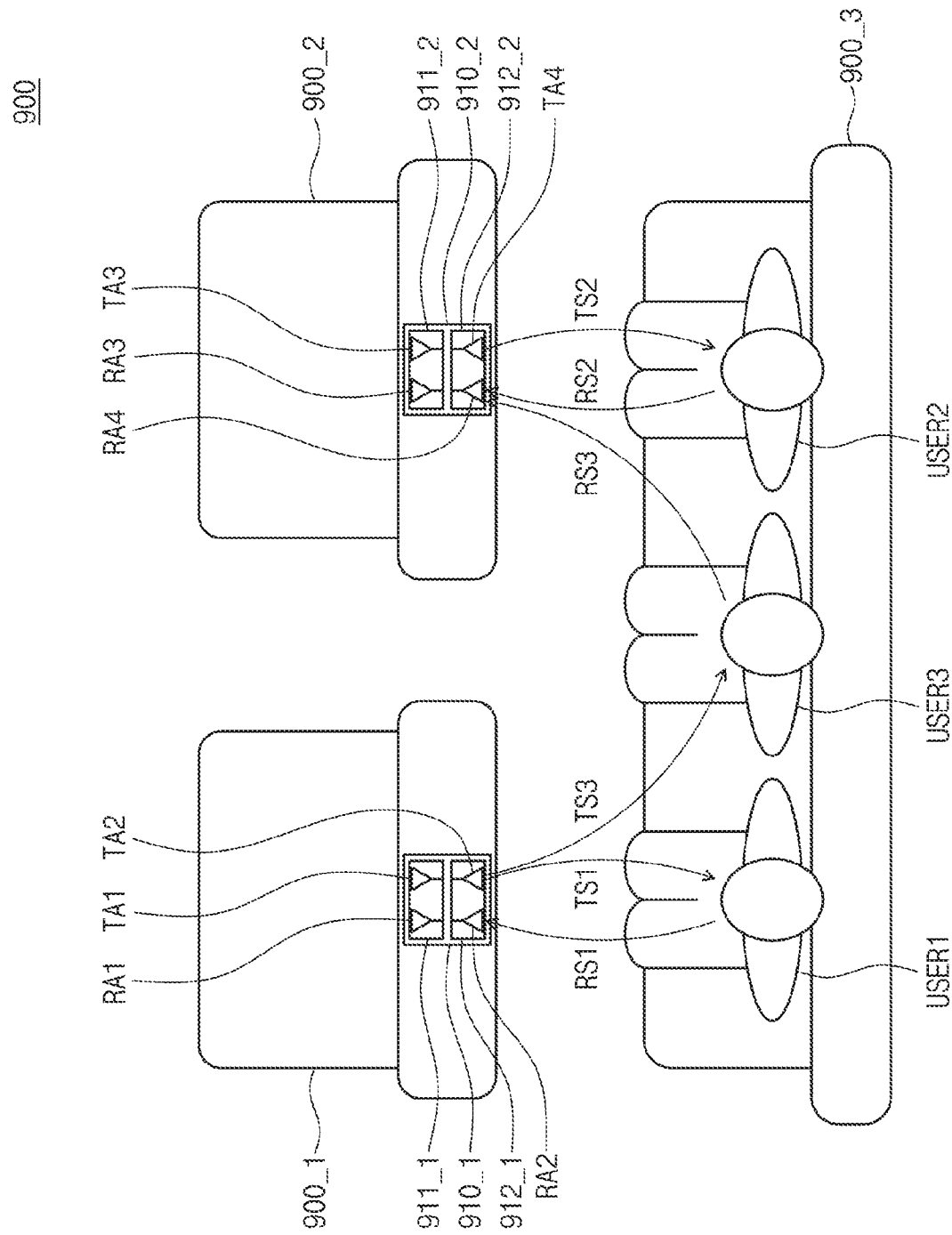
FIG. 10 is a plan view of a biosignal detecting system according to an embodiment of the inventive concept.

FIG. 10 is a plan view of a biosignal detecting device according to an embodiment of the inventive concept. Referring to FIG. 10, a biosignal detecting device 900 includes a first vehicle seat 900_1, a second vehicle seat 900_2, and a rear seat 900_3. The first vehicle seat 900_1 and the second vehicle seat 900_2 may include one of the above-described vehicle seats according to an embodiment of the inventive concept. The second vehicle seat 900_2 may be disposed at a side of the first vehicle seat 900_1. One of the first and second vehicle seats 900_1 and 900_2 may be a driver seat, and the other thereof may be a front passenger seat. The rear seat 900_3 may be disposed behind the first and second vehicle seats 900_1 and 900_2. Hereinafter, the first vehicle seat 900_1 will be described as a driver seat, and the second vehicle seat 900_2 will be described as a front passenger seat.

The first vehicle seat 900_1 includes a first biosignal detecting device 910_1. The first biosignal detecting device 910_1 includes a first antenna block 911_1 and a second antenna block 912_1. The first antenna block 911_1 may include a first transmission antenna TA1 and a first receiving antenna RA1. The second antenna block 912_2 may include a second transmission antenna TA2 and a second receiving antenna RA2. Also, the first and second antenna blocks 911_1 and 912_1 may be integrated into one antenna having a function of transmitting and receiving a signal. The first biosignal detecting device 910_1 may include a first transmitting/receiving unit connected to the first and second antenna blocks 911_1 and 912_1 and processing a transmission signal or a receiving signal to generate a biosignal.

The first antenna block 911_1 transmits the transmission signal in a front direction of the first vehicle seat 900_1 and receives a return signal. That is, the first antenna block 911_1 transmits the transmission signal to the driver and receives the return signal. On the basis of the return signal received by the first antenna block 11_1, the first biosignal detecting device 910_1 generates a biosignal of the driver. The second antenna block 912_1 transmits the transmission signal in a rear direction of the first vehicle seat 900_1 and receives the return signal. The second antenna block 912_1 may transmit the transmission signal to the person seated on the rear seat. On the basis of the return signal received by the second antenna block 912_1 from the person seated on the rear seat, the first biosignal detecting device 912_1 generates a biosignal of the person seated on the rear seat.

The second vehicle seat 900_2 includes a second biosignal detecting device 910_2. The second biosignal detecting device 910_2 includes a third antenna block 911_2 and a fourth antenna block 912_2. The third antenna block 911_2 may include a third transmission antenna TA3 and a third receiving antenna RA3. The fourth antenna block 912_2 may include a fourth transmission antenna TA4 and a fourth receiving antenna RA4. Alternatively, the third and fourth antenna blocks 911_2 and 912_2 may be integrated into one antenna having a function of transmitting and receiving a signal. The second biosignal detecting device 910_2 may include a first transmitting/receiving unit connected to the third and fourth antenna blocks 911_2 and 912_2 and processing a transmission signal or a receiving signal to generate a biosignal.

The third antenna block 911_2 transmits the transmission signal in a front direction of the second vehicle seat 900_2 and receives a return signal. That is, the third antenna block 911_2 transmits the transmission signal to the person seated on the front passenger seat and receives the return signal. On the basis of the return signal received by the third antenna block 911_2, the second biosignal detecting device 910_2 generates the biosignal of the person seated on the front passenger seat. The fourth antenna block 912_2 transmits the transmission signal in a rear direction of the second vehicle seat 900_2 and receives the return signal. The fourth antenna block 912_2 may transmit the transmission signal to the person seated on the rear seat. On the basis of the return signal received by the fourth antenna block 912_2 from the person seated on the rear seat, the second biosignal detecting device 910_2 generates the biosignal of the person seated on the rear seat.

The rear seat 900_3 may have a large area greater than that of the first vehicle seat 900_1 or the second vehicle seat 900_2 so that a plurality of persons are seated. For example, first to third seated persons USER1 to USER3 may be seated on the rear seat 900_3. The first seated person USER1 may be seated behind the first vehicle seat 900_1. The second seated person USER2 may be seated behind the second vehicle seat 900_2. The third seated person USER3 may be seated between the first and second seated persons USER1 and USER2.

The first biosignal detecting device 910_1 may generate a biosignal of the first seated person USER1. For example, the second transmission antenna TA2 may transmit a first transmission signal TS1 to the first seated person USER1, and the second receiving antenna RA2 may receive a first return signal RS1 reflected by the first seated person USER1. The first biosignal detecting device 910_1 may detect the motion of the first seated person USER1 on the basis of the first return signal RS1.

The second biosignal detecting device 910_2 may generate a biosignal of the second seated person USER2. For example, the fourth transmission antenna TA4 may transmit a second transmission signal TS2 to the second seated person USER2, and the fourth receiving antenna RA4 may receive a second return signal RS2 reflected by the second seated person USER2. The second biosignal detecting device 910_2 may detect the motion of the second seated person USER2 on the basis of the second return signal RS2.

A biosignal of the third seated person USER3 may be generated by using the first and second biosignal detecting devices 910_1 and 910_2. For example, the second transmission antenna TA2 may transmit a third transmission signal TS3 to the third seated person USER3. The fourth receiving antenna RA4 may receive a third return signal RS3 reflected by the third seated person USER3. The second biosignal detecting device 910_2 may detect the motion of the third seated person USER3 on the basis of the third return signal RS3. Alternatively, the fourth transmission antenna TA4 may transmit the third transmission signal TS3 to the third seated person USER3, and the second receiving antenna RA2 may receive the third return signal RS3. In this case, the first biosignal detecting device 910_1 may detect the motion of the third seated person USER3.

The vehicle seat transmitting the third transmission signal TS3 and the vehicle seat receiving the third return signal RS3 may be different to effectively detect the motion of the third seated person USER3 seated on an intermediate portion of the rear seat 900_3. The biosignal may be generated by mixing a detected signal generated on the basis of a local signal for generating the transmission signal and the return signal. For mixing the signals, the second biosignal detecting device 910_2 may generate the same local signal as that generated by the first biosignal detecting device 910_1. The second biosignal detecting device 910_2 may mix the generated detected signal and the local signal on the basis of the third return signal RS3.

Although the first and second vehicle seats 900_1 and 900_2 respectively include the biosignal detecting devices different from each other, an embodiment of the inventive concept is not limited thereto. For example, the first vehicle seat 900_1 includes the first and second antenna blocks 911_1 and 912_1. The second vehicle seat 900_2 includes the third and fourth antenna blocks 911_2 and 912_2. Here, other components except for the antenna blocks, e.g., the signal transmitting/receiving unit 142 and the switch unit 143 in FIG. 2, may be shared in common. That is, the transmission signal for detecting the motion of various seated persons may be generated on the basis of the same oscillator. Alternatively, the biosignals of various seated persons may be generated by mixing the local signal generated by the same oscillator with the detected signal of the seated persons.

The rear seat 900_3 may not include the biosignal detecting device or the antenna block for detecting the motion of the first to third seated persons USER1 to USER3. That is, since the biosignals of the first to third seated persons USER1 to USER3 are generated by using the first biosignal detecting device 910_1 provided in the first vehicle seat 900_1 and the second biosignal detecting device 910_2 provided in the second vehicle seat 900_2, an additional electronic device is not required to be disposed in the rear seat 900_3. Also, the biosignal of the third seated person USER3 seated on the intermediate portion of the rear seat 900_3 may be easily generated without an additional biosignal detecting device. Thus, the biosignal detecting system 900 improves in efficiency and convenience of design.

Figure 11:
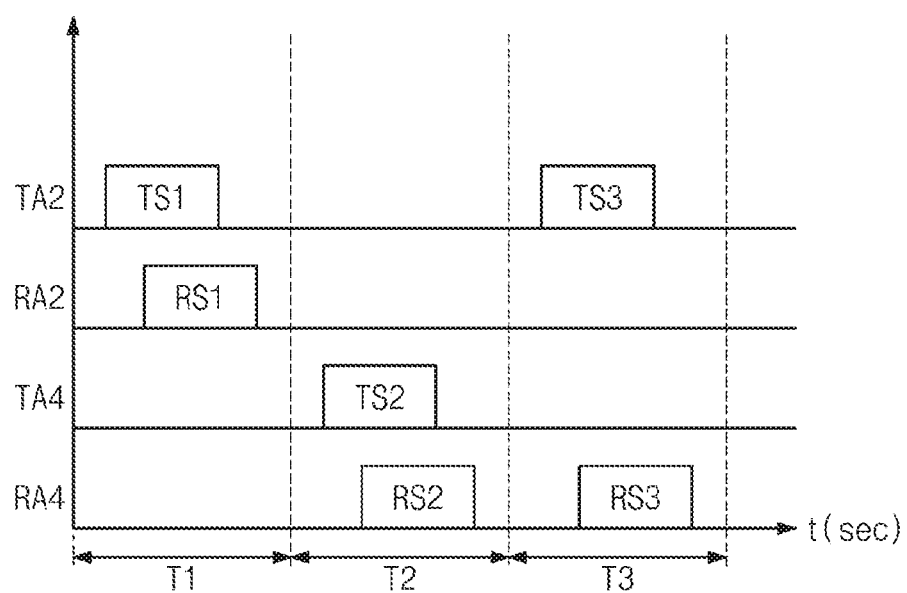
FIG. 11 is a timing chart for explaining biosignal detection of first to third seated persons in FIG. 10.

FIG. 11 is a timing chart for explaining biosignal detection of the first to third seated persons in FIG. 10. Referring to FIG. 11, a horizontal axis represents a flow of time. The biosignal detecting system 900 in FIG. 10 may detect the motion of the first to third seated persons USER1 to USER3 by using a time division method. A vertical axis represents activation or deactivation of each of the second transmission antenna TA2, the second receiving antenna RA2, the fourth transmission antenna TA3, and the fourth receiving antenna RA4. That is, the vertical axis represents that the antenna block transmits the transmission signal ore receives the return signal.

During a first period T1, the biosignal detecting system 9000 in FIG. 10 may detect the motion of the first seated person USER1. During the first period T1, the second transmission antenna TA2 transmits the first transmission signal TS1 to the first seated person USER1. The second receiving antenna RA2 receives the first return signal RS1 in response to the first transmission signal TS1. As much as a time in which the first transmission signal TS1 is reflected to be returned to the first seated person USER1, a receiving time of the first return signal RS1 is delayed.

During a second period T2, the biosignal detecting system 9000 in FIG. 10 may detect the motion of the second seated person USER2. During the second period T2, the fourth transmission antenna TA4 transmits the second transmission signal TS2 to the second seated person USER2. The fourth receiving antenna RA4 receives the second return signal RS2 in response to the second transmission signal TS2. As much as a time in which the second transmission signal TS2 is reflected to be returned to the second seated person USER2, a receiving time of the second return signal RS2 is delayed.

During a third period T3, the biosignal detecting system 9000 in FIG. 10 may detect the motion of the third seated person USER3. During the third period, the second transmission antenna TA2 transmits the third transmission signal TS3 to the third seated person USER3. The fourth receiving antenna RA4 receives the third return signal RS3 in response to the third transmission signal TS3. As much as a time in which the third transmission signal TS3 is reflected to be returned to the third seated person USER3, a receiving time of the third return signal RS3 is delayed.

Figure 12:
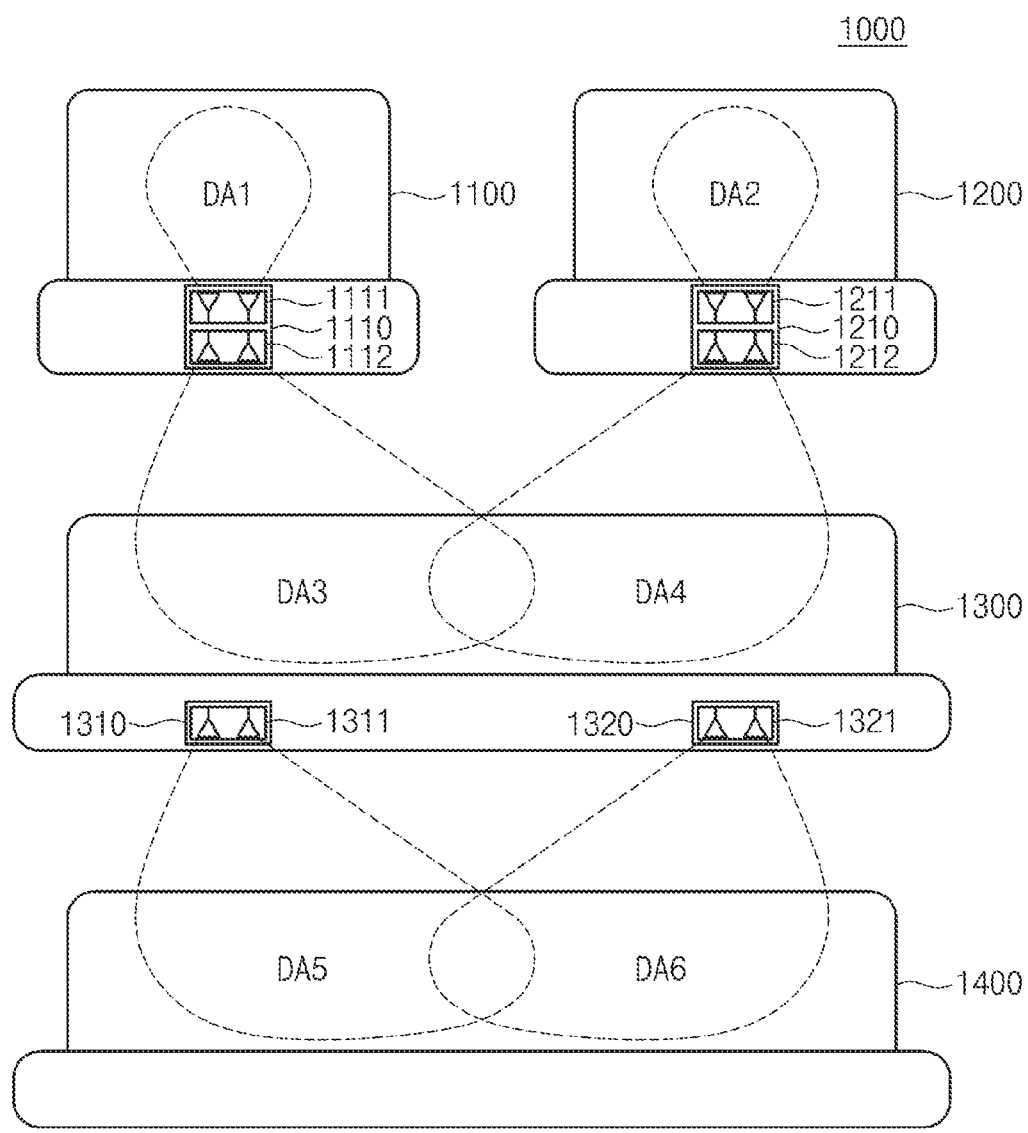
FIG. 12 is a plan view of a biosignal detecting system according to an embodiment of the inventive concept.

FIG. 12 is a plan view of a biosignal detecting system according to an embodiment of the inventive concept. Referring to FIG. 12, a biosignal detecting system 1000 includes a first vehicle seat 1100, a second vehicle seat 1200, a first rear seat 1300, and a second rear seat 1400. The first vehicle seat 1100 may have the same constitution as that of the first vehicle seat 900_1 in FIG. 10. The second vehicle seat 1200 may have the same constitution as that of the second vehicle seat 900_2 in FIG. 10. The first rear seat 1300 may be disposed behind the first and second vehicle seats 1100 and 1200. The second rear seat 1400 may be disposed behind the first rear seat 1300. The biosignal detecting system 1000 in FIG. 12 may be applied to a high-occupancy vehicle such as a van.

The first vehicle seat 1100 includes a first biosignal detecting device 1110. The first biosignal detecting device 1110 includes a first antenna block 1111 and a second antenna block 1112. The first antenna block 1111 transmits a transmission signal in a front direction of the first vehicle seat 1100 and receives a return signal. That is, a biosignal of a person seated in a first detection region DA1 is generated by using the first antenna block 1111. The second antenna block 1112 transmits a transmission signal in a rear direction of the first vehicle seat 1100 and receives a return signal. That is, a biosignal of a person seated in a third detection region DA3 is generated by using the second antenna block 1112.

The second vehicle seat 1200 includes a second biosignal detecting device 1210. The second biosignal detecting device 1210 includes a third antenna block 1211 and a fourth antenna block 1212. The third antenna block 1211 transmits a transmission signal in a front direction of the second vehicle seat 1200 and receives a return signal. That is, a biosignal of a person seated in a second detection region DA2 is generated by using the third antenna block 1211. The fourth antenna block 1212 transmits a transmission signal in a rear direction of the second vehicle seat 1200 and receives a return signal. That is, a biosignal of a person seated in a fourth detection region DA4 is generated by using the fourth antenna block 1212.

A plurality of persons may be seated on the first rear seat 1300. A biosignal of a person seated behind the first vehicle seat 1100, i.e., in a third detection region DA3, may be generated by using the first biosignal detecting device 1110. A biosignal of a person seated behind the second vehicle seat 1200, i.e., in a fourth detection region DA4, may be generated by using the second biosignal detecting device 121. A biosignal of a person seated on an intermediate portion of the first rear seat 1300, i.e., in a region in which the third detection region DA3 and the fourth detection region DA4 overlap each other, may be generated by using the first and second biosignal detecting devices 1110 and 1210. For example, as the second antenna block 1112 transmits a transmission signal, and the fourth antenna block 1212 receives a return signal, the biosignal may be generated.

The first rear seat 1300 includes a third biosignal detecting device 1310 and a fourth biosignal detecting device 1320. The third biosignal detecting device 1310 includes a fifth antenna block 1311. The fourth biosignal detecting device 1320 includes a sixth antenna block 1321. The fifth and sixth antenna blocks 1311 and 1321 may transmit a transmission signal in a rear direction of the first rear seat 1300 and receive a return signal. That is, a biosignal of a person seated in a fifth detection region DA5 is generated by using the fifth antenna block 1311. Also, a biosignal of a person seated in a sixth detection region DA6 is generated by using the sixth antenna block 1321.

A plurality of persons may be seated on the second rear seat 1400. A biosignal of a person seated in a region of the fifth detection region DA5, which does not overlap the sixth detection region DA6, may be generated by using the third biosignal detecting device 1310. A biosignal of a person seated in a region of the sixth detection region DA6, which does not overlap the fifth detection region DA5, may be generated by using the fourth biosignal detecting device 1320. A biosignal of a person seated in a region in which the fifth detection region DA5 and the sixth detection region DA6 overlap each other may be generated by using the third and fourth biosignal detecting devices 1310 and 1320. For example, as the fifth antenna block 1311 transmits a transmission signal, and the sixth antenna block 1321 receives a return signal, the biosignal may be generated.

The second rear seat 1400 may not include an additional biosignal detecting device. That is, since biosignals of persons seated on the second rear seat 1400 are generated by using the first rear seat 1300, an additional electronic device is not required to be disposed in the second rear seat 1400. Thus, the biosignal detecting system 1000 improves in efficiency and convenience of design. Unlike FIG. 12, the third biosignal detecting device 1310 and the fourth biosignal detecting device 1320 may be included in the second rear seat 1400. In this case, the third and fourth biosignal detecting devices 1310 and 1320 may transmit a transmission signal in a front direction of the second rear seat 1400. Also, the first rear seat 1300 may not include an additional biosignal detecting device.

Each of the third to sixth detection regions DA3 to DA6 may be greater in area than each of the first and second detection region DA1 and DA2. The reason is that a distance between the person seated on the first rear seat 1300 and the second antenna block 1112 (or fourth antenna block 1212) is greater than a distance between the person seated on the first vehicle seat 1100 (or second vehicle seat 1200) and the first antenna block 1111 (or third antenna block 1211). Accordingly, energy of the transmission signal provided from the second antenna block 1112 or the fourth antenna block 1212 may be less than that of the transmission signal provided from the first antenna block 1111 or the third antenna block 1211.

Figure 13:
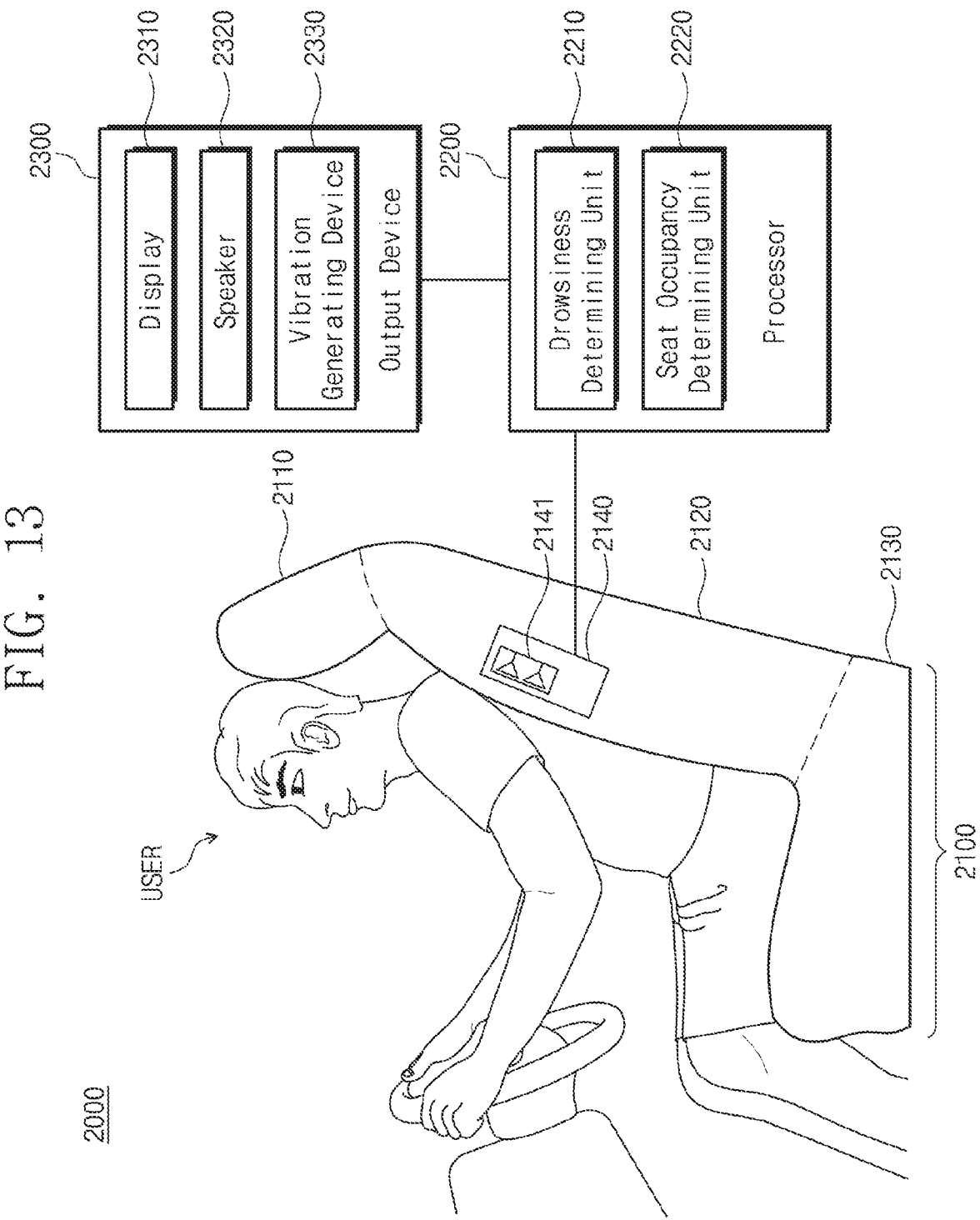
FIG. 13 is a view of a biosignal detecting system according to an embodiment of the inventive concept.

FIG. 13 is a view of a biosignal detecting system according to an embodiment of the inventive concept. Referring to FIG. 13, a biosignal detecting system 2000 includes a vehicle seat 2100, a processor 2200, and an output device 2300. The vehicle seat 2100 includes a head support part 2110, a backrest part 2120, a bottom part 2130, and a biosignal detecting device 2140. The biosignal detecting device 2140 includes an antenna block 2141. The vehicle seat 2100 may include one of the vehicle seats described in FIGS. 1 to 9.

The processor 2200 may perform a function of a central control device of the biosignal detecting system 2000. The processor 2200 may perform a control operation and a calculation operation, which are required to realize the biosignal detecting system 2000. For example, the biosignal detecting device 2140 included in the vehicle seat 2100 may transmit a transmission signal to the seated person USER and receive a return signal according to the control of the processor. The biosignal detecting device 2140 may generate a biosignal according to the control of the processor 2200. The processor 2200 may include a drowsiness determining unit 2210 and a seat occupancy determining unit 2200.

The drowsiness determining unit 2210 may receive a biosignal from the biosignal detecting device 2140 according to the control of the processor 2200. The drowsiness determining unit 2210 may determine whether the seated person USER is drowsy on the basis of the biosignal. The biosignal may include information on breath or heartbeat of the seated person USER on the basis of motion of the seated person USER. The drowsiness determining unit 2210 may determine a heartbeat rate, a heartbeat variation rate, a breath rate, or a breath size of the seated person USER on the basis of the biosignal. The drowsiness determining unit 2210 may predict a sleeping state or a drowsing state of the seated person USER by analyzing the heartbeat rate, the heartbeat variation rate, the breath rate, the breath size, or the like. The drowsiness determining unit 2210 may be realized by using an individual circuit such as application specific integrated circuit (ASIC). Alternatively, the drowsiness determining unit 2210 may be realized by a software or a firmware to determine whether the seated person USER is drowsy.

When the drowsiness determining unit 2210 determines that the seated person is in a drowsiness state on the basis of an analysis result of the biosignal, a drowsiness signal may be generated. The drowsiness warning signal may be provided to the output device 2300. When the drowsiness signal is received, the output device 2300 may display a drowsiness warning screen, generate a drowsiness prevention alarm, or generate a vibration. The drowsiness determining unit 2210 may receive the biosignal from the biosignal detecting device included in the driver seat to determine whether the driver is drowsy. That is, the drowsiness determining unit 2210 may determine whether the driver drives while drowsy. Also, the drowsiness determining unit 2210 may receive the biosignal from the front passenger seat or the rear seat to determine the drowsiness state. For example, when the biosignal detecting system 2000 is an autonomous driving system and is reached to a destination, the drowsiness determining unit 2210 may generate the drowsiness signal.

The seat occupancy determining unit 2220 may receive the biosignal from the biosignal detecting device 2140 according to the control of the processor 2200. The seat occupancy determining unit 2220 may determine whether the seated person USER occupies the seat on the basis of the biosignal. The biosignal detecting device 2140 generates the biosignal on the basis of the motion of the seated person USER. When the seated person USER is not seated on the vehicle seat 2100, the biosignal detecting device 2140 may not detect the motion. Accordingly, the seat occupancy determining unit 2220 may predict whether the seat is occupied by the seated person USER by analyzing the biosignal. The seat occupancy determining unit 2220 may be realized by using an individual circuit such as application specific integrated circuit (ASIC). Alternatively, the seat occupancy determining unit 2220 may be realized by a software or a firmware to determine whether the seat is occupied by the seated person USER.

The seat occupancy determining unit 2220 may analyze the biosignal to generate a seat occupancy signal. The seat occupancy signal may be provided to the output device 2300. When the seat occupancy signal is received, the output device 2300 may display an occupancy indication or the like. Alternatively, the output device 2300 may generate a seat occupancy guidance alarm or display a seat occupancy guidance screen. The seat occupancy determining unit 2220 may receive the biosignal from the driver seat, the front passenger seat, and the rear seat to determine whether the seat is occupied. When the processor 2200 recognizes that the seated person USER is seated on the vehicle seat 2100, the processor 2200 may determine whether a safety belt is fastened and provide information on safety belt fastening to the output device.

The seat occupancy determining unit 2220 may analyze the biosignal to determine the kinds of an object occupying the vehicle seat 2100. For example, when the object occupying the vehicle seat 2100 is an inanimate object, the biosignal detecting device 2140 may not detect motion of the object. In this case, the seat occupancy determining unit 2220 may determine that the object is an inanimate object, so that the seat occupancy signal is not generated. Also, when the object occupying the vehicle seat 2100 is an animal such as a dog, the biosignal generated by the biosignal detecting device 2140 may be different from the biosignal generated by a human. That is, since heartbeat and breath of an animal is different from those of a human, the seat occupancy determining unit 2220 may determine that the object occupying the vehicle seat 2100 is not a human.

The processor 2200 may receive the biosignal to generate a signal related to the various seated person USER in addition to the drowsiness or the seat occupancy. For example, the processor 2200 may analyze the biosignal to determine whether a sudden disease occurs. The processor 2200 may determine a health condition of the seated person USER when a vehicle accident occurs. The processor 2200 may control vehicle driving in addition to the biosignal processing and various devices, e.g., the seat fan or the heating wire, included in the biosignal detecting system 2000.

The output device 2300 may receive various signals from the processor 2300. The output device 2300 may output various information that is recognizable by the seated person USER according to the control of the processor 2200. The output device 2300 may receive the drowsiness warning signal generated by the drowsiness determining unit 2210. The output device 2300 may receive the seat occupancy signal generated by the seat occupancy determining unit 2220. The output device 2300 may include a display 2310, a speaker 2320, and a vibration generating device 2330.

The display 2310 may display an image on the basis of the signal received from the processor 2200. For example, the display 2310 may display the drowsiness warning screen on the basis of the drowsiness warning signal. The display 2310 may display the seat occupancy guidance screen on the basis of the seat occupancy signal. The speaker 2320 may generate a sound on the basis of the signal received from the processor 2200. For example, the speaker 2320 may generate the drowsiness prevention alarm on the basis of the drowsiness warning signal. The speaker 2320 may display the seat occupancy guidance alarm on the basis of the seat occupancy signal. The vibration generating device 2330 may generate a vibration on the basis of the signal received from the processor 2200. For example, the vibration generating device 2330 may generate a vibration on the basis of the drowsiness warning signal.

The biosignal detecting system 2000 may further include a memory for storing information and codes, which are processed or will be processed by the processor 2200. The memory may store the biosignal generated by the biosignal detecting device or the like. Also, the biosignal detecting system 2000 may further include a storage for storing information generated by an operating system or applications, a file for driving the operating system, or an execution file of the applications, which are intended to be stored for a long-term. Besides, the biosignal detecting system 2000 may further include various components for performing functions of the biosignal detecting system 2000.

Figure 14:
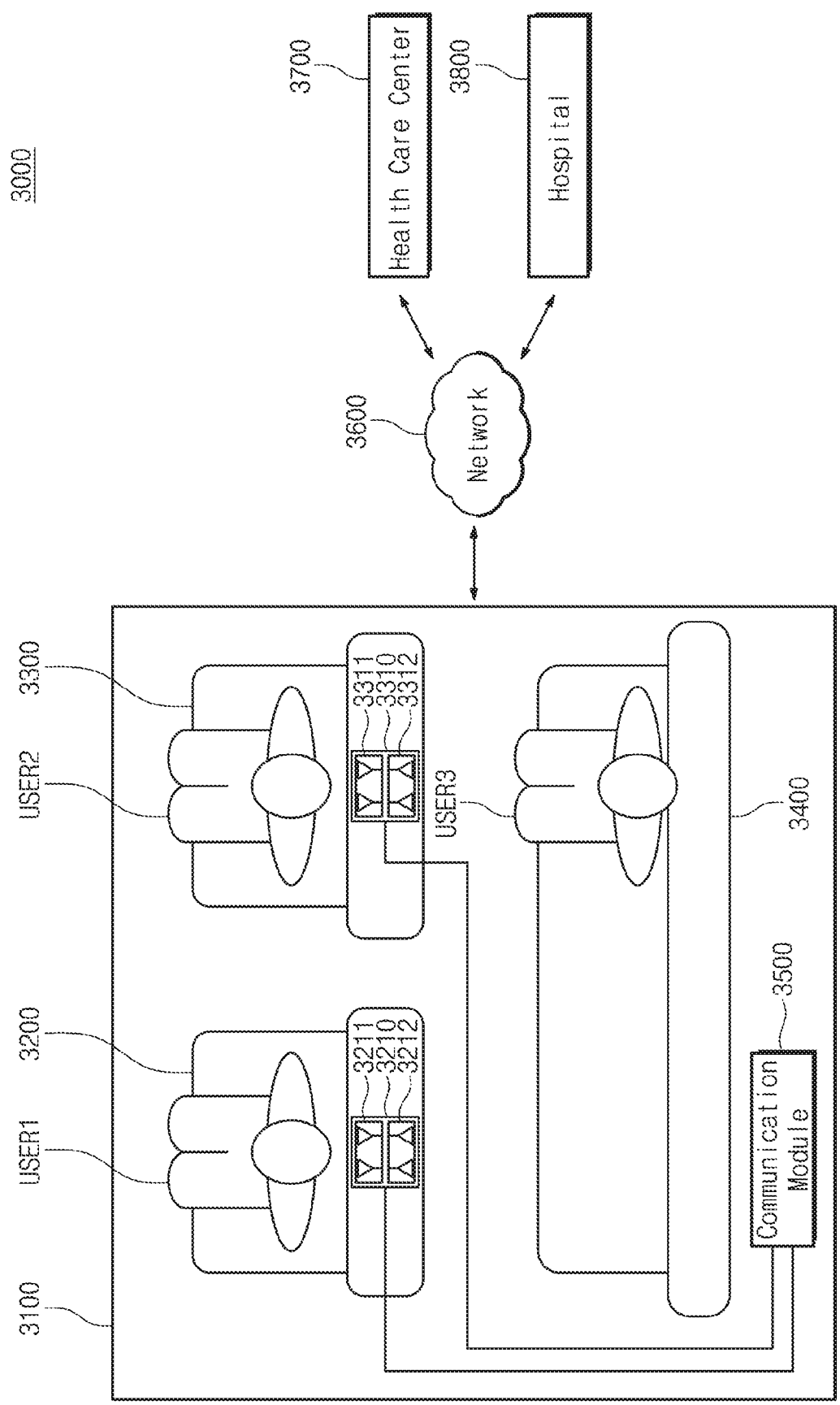
FIG. 14 is a view of a health care system according to an embodiment of the inventive concept.

FIG. 14 is a view of a health care system according to an embodiment of the inventive concept. Referring to FIG. 14, a health care system 3000 may include a biosignal detecting system 3100, a network 3600, a health care center 3700, and a hospital 3800. The biosignal detecting system 3100 may include a first vehicle seat 3200, a second vehicle seat 3300, a rear seat 3400, and a communication module 3500.

The first vehicle seat 3200 may include a first biosignal detecting device 3210. The first biosignal detecting device 3210 may include a first antenna block 3211 and a second antenna block 3212. The second vehicle seat 3300 includes a second biosignal detecting device 3310. The second biosignal detecting device 3310 may include a third antenna block 3311 and a fourth antenna block 3312. The first vehicle seat 3200 may have the same constitution as that of the first vehicle seat 900_1 in FIG. 10. The second vehicle seat 3300 may have the same constitution as that of the second vehicle seat 900_2 in FIG. 10. The rear seat 3400 may have the same constitution as that of the rear seat 900_3 in FIG. 10.

The communication module 3500 may receive the biosignals of a driver, a person seated on a front passenger seat, and a person seated on a rear seat from the first and second biosignal detecting devices 3210 and 3310. The communication module 3500 may generate the biosignal of the passenger on the basis of the biosignal. The communication module 3500 may encode the biosignal to generate the biosignal of the passenger. The communication module 3500 may transmit the biosignal of the passenger through a wire or a wireless communication.

The network 3600 may receive the biosignal of the passenger from the communication module 3500 and provide the received biosignal to the health care center 3700 or the hospital 3800. The health care center 3700 or the hospital 3800 may provide a health care service on the basis of the biosignal of the passenger. For example, the health care center 3700 may monitor a health state of the passengers using the biosignal detecting system 3100 on the basis of the biosignal of the passenger. The health care center 3700 may provide a health care signal to the biosignal detecting system 3100 through the network 3600. The hospital 3800 may recognize whether the seated persons using the biosignal detecting system 3100 have diseases on the basis of the biosignal of the passenger. The hospital 3800 may provide a health warning signal through the network 3600. Besides, the biosignal of the passenger may be provided to various service providing facilities through the network 3600.

The biosignal detecting device and the biosignal detecting system including the same according to the embodiment of the inventive concept may be built in the vehicle seat to detect the motion of the seated person, thereby exactly and effectively detecting the biosignal. Also, the biosignal detecting device and the biosignal detecting system including the same according to the embodiment of the inventive concept may effectively detect the biosignals of the seated persons boarding on the vehicle in virtue of arranging the optimized biosignal detecting device and provide various services by using the detected biosignals.

The above-described contents are exemplary embodiments for implementing the present disclosure. Although the exemplary embodiments of the present invention have been described, it is understood that the present disclosure should not be limited to these exemplary embodiments but various changes and modifications can be made by one ordinary skilled in the art within the spirit and scope of the present invention as hereinafter claimed.

What is claimed is:

1. A biosignal detecting device that is built in a vehicle seat, comprising:
   an antenna block, which is built in a backrest part of the vehicle seat, configured to transmit a transmission signal to a person seated on the vehicle seat and receive a return signal corresponding to the transmission signal,
   wherein one surface of the backrest part, which contacts the seated person, and the antenna block are spaced apart from each other so that a distance between the one surface and the antenna block built in the backrest part is at least two times or more greater than a wavelength of the transmission signal.

2. The biosignal detecting device of claim 1, further comprising:
   an oscillator configured to generate a local signal having the same frequency as that of the transmission signal; and
   a mixer configured to mix the local signal with a detected signal generated on the basis of the return signal.

3. The biosignal detecting device of claim 1, wherein the antenna block comprises:
   a transmission antenna configured to emit the transmission signal; and
   a receiving antenna configured to receive the return signal.

4. The biosignal detecting device of claim 1, further comprising:
   a signal transmitting/receiving unit configured to generate first and second transmission signals and receive first and second return signals to generate a biosignal; and
   a switch unit configured to electrically connect a first antenna block configured to transmit the first transmission signal and receive the first return signal to the signal transmitting/receiving unit or electrically connect a second antenna block configured to transmit the second transmission signal and receive the second return signal to the signal transmitting/receiving part.

5. The biosignal detecting device of claim 1, wherein the antenna block is disposed adjacent to a wave absorber that is disposed to absorb a transmission signal transmitted to a seat fan comprising a rotating blade.

6. The biosignal detecting device of claim 5, wherein the antenna block is disposed adjacent to a first wave absorber disposed to absorb a transmission signal transmitted to a first seat fan and disposed adjacent to a second wave absorber disposed to absorb a transmission signal transmitted to a second seat fan.

7. The biosignal detecting device of claim 1, wherein the antenna block is spaced apart from a heating wire built in the vehicle seat.

8. The biosignal detecting device of claim 1, wherein the antenna block contacts a separation member provided between the one surface and the antenna block and is spaced apart from the one surface so that a distance therebetween is two times or more greater than the wavelength of the transmission signal.

9. The biosignal detecting device of claim 1, wherein the antenna block contacts one surface of the vehicle seat having a groove, and the groove has a depth that is two times or more greater than the wavelength of the transmission signal.

10. The biosignal detecting device of claim 1, further comprising a signal transmitting/receiving unit configured to generate a biosignal on the basis of a phase difference between the transmission signal and the return signal.

11. The biosignal detecting device of claim 1, further comprising a signal transmitting/receiving unit configured to generate a biosignal on the basis of a transmitting time of the transmission signal and a receiving time of the return signal.

* * * * *